United States Patent
Kuhn et al.

(10) Patent No.: US 8,634,890 B2
(45) Date of Patent: Jan. 21, 2014

(54) DEVICE AND METHOD FOR MONITORING OF ABSOLUTE OXYGEN SATURATION AND TISSUE HEMOGLOBIN CONCENTRATION

(75) Inventors: Jonathan L. Kuhn, Ham Lake, MN (US); Can Cinbis, Shoreview, MN (US); James K. Carney, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 698 days.

(21) Appl. No.: 12/797,744

(22) Filed: Jun. 10, 2010

(65) Prior Publication Data

US 2010/0317938 A1     Dec. 16, 2010

Related U.S. Application Data

(60) Provisional application No. 61/185,818, filed on Jun. 10, 2009.

(51) Int. Cl.
*A61B 5/00* (2006.01)
(52) U.S. Cl.
USPC .......................................... 600/323; 600/310
(58) Field of Classification Search
USPC .................................... 600/310, 323
See application file for complete search history.

(56) References Cited

U.S. PATENT DOCUMENTS

| | | | |
|---|---|---|---|
| 4,180,078 A | 12/1979 | Anderson | |
| 4,202,339 A | 5/1980 | Wirtzfeld et al. | |
| 4,230,122 A | 10/1980 | Lubbers et al. | |
| 4,399,820 A | 8/1983 | Wirtzfeld et al. | |
| 4,467,807 A | 8/1984 | Bornzin | |
| 4,548,209 A | 10/1985 | Wielders et al. | |
| 4,567,892 A | 2/1986 | Piocchi et al. | |
| 4,750,495 A | 6/1988 | Moore et al. | |
| 4,967,748 A | 11/1990 | Cohen | |
| 5,007,423 A | 4/1991 | Branstetter et al. | |

(Continued)

FOREIGN PATENT DOCUMENTS

| EP | 760476 | 3/1997 |
|---|---|---|
| EP | 1764034 | 3/2007 |

(Continued)

OTHER PUBLICATIONS

Myers, Dean E., Noninvasive Method for Measuring Local Hemoglobin Oxygen Saturation in Tissue Using Wide Gap Second Derivative Near-Infrared Spectroscopy, Journal of Biomedical Optics 10(3), 034017 (May/Jun. 2005).

(Continued)

*Primary Examiner* — Clayton E Laballe
*Assistant Examiner* — Warren K Fenwick
(74) *Attorney, Agent, or Firm* — Evans M. Mburu; Stephen W. Bauer

(57) ABSTRACT

A method and medical device for detecting signals that detects emitted light scattered by a volume of tissue delivered along a first pathway at a plurality of wavelengths to generate corresponding first detected light intensity output signals, detects emitted light scattered by the volume of tissue delivered along a second pathway different from the first pathway at a plurality of wavelengths to generate corresponding second detected light intensity output signals, determines whether a difference between the emitted light detected along the first pathway and the emitted light detected along the second pathway is greater than a predetermined threshold, and alters sensing by the device in response to the determining whether a difference is greater than the predetermined threshold.

12 Claims, 14 Drawing Sheets

(56) References Cited

U.S. PATENT DOCUMENTS

| | | | |
|---|---|---|---|
| 5,163,427 A | 11/1992 | Keimel | |
| 5,176,137 A | 1/1993 | Erickson et al. | |
| 5,188,105 A | 2/1993 | Keimel | |
| 5,188,108 A | 2/1993 | Secker | |
| 5,193,535 A | 3/1993 | Bardy et al. | |
| 5,213,098 A | 5/1993 | Bennett | |
| 5,218,962 A * | 6/1993 | Mannheimer et al. | 600/331 |
| 5,227,181 A | 7/1993 | Knudsen | |
| 5,354,316 A | 10/1994 | Keimel | |
| 5,364,316 A | 11/1994 | Brambilla | |
| 5,385,143 A | 1/1995 | Aoyagi | |
| 5,398,680 A | 3/1995 | Polson et al. | |
| 5,431,172 A | 7/1995 | Hoegnelid et al. | |
| 5,464,434 A | 11/1995 | Alt | |
| 5,470,345 A | 11/1995 | Hassler et al. | |
| 5,531,714 A | 7/1996 | Dahn et al. | |
| 5,545,186 A | 8/1996 | Olson et al. | |
| 5,588,427 A | 12/1996 | Tien | |
| 5,593,431 A | 1/1997 | Sheldon | |
| 5,596,986 A | 1/1997 | Goldfarb | |
| 5,683,432 A | 11/1997 | Goedeke et al. | |
| 5,725,219 A | 3/1998 | Gilbert | |
| 5,752,519 A | 5/1998 | Benaron et al. | |
| 5,769,785 A | 6/1998 | Diab et al. | |
| 5,855,593 A | 1/1999 | Olson et al. | |
| 5,879,294 A | 3/1999 | Anderson et al. | |
| 5,902,326 A | 5/1999 | Lessar et al. | |
| 6,144,866 A | 11/2000 | Miesel et al. | |
| 6,198,952 B1 | 3/2001 | Miesel et al. | |
| 6,226,540 B1 | 5/2001 | Bernreuter | |
| 6,236,882 B1 | 5/2001 | Lee et al. | |
| 6,292,698 B1 | 9/2001 | Duffin et al. | |
| 6,377,840 B1 | 4/2002 | Gritsenko et al. | |
| 6,473,632 B1 | 10/2002 | Myers | |
| 6,481,899 B1 | 11/2002 | Quast et al. | |
| 6,487,343 B1 | 11/2002 | Lewandowski et al. | |
| 6,512,940 B1 | 1/2003 | Brabec et al. | |
| 6,522,915 B1 | 2/2003 | Ceballos et al. | |
| 6,587,703 B2 * | 7/2003 | Cheng et al. | 600/310 |
| 6,599,250 B2 | 7/2003 | Webb et al. | |
| 6,615,064 B1 | 9/2003 | Aldrich | |
| 6,622,046 B2 | 9/2003 | Fraley et al. | |
| 6,667,803 B1 | 12/2003 | Flessland et al. | |
| 6,682,135 B2 | 1/2004 | Zheng | |
| 6,738,667 B2 | 5/2004 | Deno et al. | |
| 6,839,583 B1 | 1/2005 | Lewandowski et al. | |
| 6,839,592 B2 | 1/2005 | Grandjean | |
| 6,850,787 B2 | 2/2005 | Weber et al. | |
| 6,892,006 B2 | 5/2005 | Lewandowski et al. | |
| 6,944,488 B2 | 9/2005 | Roberts | |
| 6,997,879 B1 | 2/2006 | Turcott | |
| 7,043,294 B1 | 5/2006 | Paris | |
| 7,096,064 B2 | 8/2006 | Deno et al. | |
| 7,127,278 B2 * | 10/2006 | Melker et al. | 600/340 |
| 7,164,948 B2 | 1/2007 | Struble et al. | |
| 7,165,893 B2 | 1/2007 | Schmitz | |
| 7,177,686 B1 | 2/2007 | Turcott | |
| 7,239,385 B2 | 7/2007 | Schmitz et al. | |
| 7,239,901 B2 | 7/2007 | Gritsenko | |
| 7,277,757 B2 | 10/2007 | Casavant et al. | |
| 7,302,294 B2 | 11/2007 | Kamath et al. | |
| 7,809,441 B2 | 10/2010 | Kane et al. | |
| 7,991,448 B2 | 8/2011 | Edgar, Jr. et al. | |
| 8,038,626 B2 | 10/2011 | Cinbis et al. | |
| 8,055,321 B2 | 11/2011 | Bernreuter | |
| 8,090,432 B2 | 1/2012 | Cinbis et al. | |
| 8,165,662 B2 | 4/2012 | Cinbis et al. | |
| 2003/0004412 A1 | 1/2003 | Izatt et al. | |
| 2003/0065365 A1 | 4/2003 | Zhu et al. | |
| 2003/0144584 A1 | 7/2003 | Mendelson | |
| 2003/0187480 A1 | 10/2003 | KenKnight et al. | |
| 2003/0199956 A1 | 10/2003 | Strubble | |
| 2004/0024297 A1 | 2/2004 | Chen et al. | |
| 2004/0220629 A1 | 11/2004 | Kamath et al. | |
| 2005/0119586 A1 | 6/2005 | Coyle et al. | |
| 2005/0148832 A1 | 7/2005 | Reghabi et al. | |
| 2005/0277818 A1 * | 12/2005 | Myers | 600/323 |
| 2006/0009685 A1 | 1/2006 | Finarov et al. | |
| 2006/0025827 A1 | 2/2006 | Hatlesad et al. | |
| 2006/0106293 A1 | 5/2006 | Fantini | |
| 2006/0253007 A1 | 11/2006 | Cheng et al. | |
| 2007/0203406 A1 | 8/2007 | Anderson et al. | |
| 2007/0239052 A1 * | 10/2007 | Bhunia | 600/513 |
| 2007/0239053 A1 * | 10/2007 | Bhunia | 600/513 |
| 2007/0239215 A1 | 10/2007 | Bhunia et al. | |
| 2007/0255148 A1 * | 11/2007 | Bhunia | 600/509 |
| 2008/0004513 A1 | 1/2008 | Walker et al. | |
| 2008/0015424 A1 | 1/2008 | Bernreuter | |
| 2008/0103538 A1 | 5/2008 | Walker et al. | |
| 2008/0208011 A1 * | 8/2008 | Shuler | 600/301 |
| 2008/0208020 A1 * | 8/2008 | Cinbis et al. | 600/323 |
| 2008/0208269 A1 | 8/2008 | Cinbis et al. | |
| 2008/0306390 A1 * | 12/2008 | Cinbis | 600/477 |
| 2010/0130840 A1 * | 5/2010 | Isaacson | 600/323 |
| 2010/0185252 A1 | 7/2010 | Bjorling et al. | |
| 2010/0292548 A1 | 11/2010 | Baker, Jr. et al. | |
| 2010/0292549 A1 * | 11/2010 | Shuler | 600/324 |
| 2010/0317943 A1 | 12/2010 | Kuhn et al. | |
| 2011/0066017 A1 | 3/2011 | Kuhn | |

FOREIGN PATENT DOCUMENTS

| | | |
|---|---|---|
| EP | 1955653 | 8/2008 |
| GB | 1419701 | 12/1975 |
| WO | 9825669 | 6/1998 |
| WO | 03077750 | 9/2003 |
| WO | 2004091719 | 10/2004 |
| WO | 2007012931 | 2/2007 |
| WO | 2008105698 | 9/2008 |
| WO | 2008118042 | 10/2008 |
| WO | 2008151263 | 12/2008 |

OTHER PUBLICATIONS

Benaron, David A., Quantitative Clinical Non-Pulsatile and Localized Visible Light Oximter: Design of the T-Stat (Trade Market) Tissue Oximeter, Stanford University School of Medicine, Palo Alto, CA USA 94305.

(PCT/US2010/038119) PCT Notification of Transmittal of the International Search Report and the Written Opinion of the International Searching Authority, Mailed Sep. 1, 2010, 10 pages.

St Jude Medical, ME 317: Design for Manufacturability, Implantable Pulse Generator Optical Sensing System, Jun. 1, 2004, 225 pages.

M.N. Ericson et al., Development of an Implantable Oximetry-Based Organ Perfusion Sensor, Proceeding of the 26th Annual International Conference of the IEEE EMBS, Sep. 1-5, 2004, pp. 2235-2238.

JR Wilson et al., Noninvasive Detection of Skeletal Muscle Underperfusion with Near-Infrared Spectroscopy ion Patients with Heart Failure; Circulation: Journal of the American Heart Association, 1989;80; pp. 1668-1674.

Benaron, David A., Quantitative Clinical Non-Pulsatile and Localized Visible Light Oximter: Design of the T-Stat (Trade Market) Tissue Oximeter, Stanford University School of Medicine, Palo Alto, CA USA 94305, Jul. 30, 2003.

* cited by examiner

US 8,634,890 B2

DEVICE AND METHOD FOR MONITORING OF ABSOLUTE OXYGEN SATURATION AND TISSUE HEMOGLOBIN CONCENTRATION

RELATED PRIORITY APPLICATION

The present application claims priority and other benefits from U.S. Provisional Patent Application Ser. No. 61/185,818, filed Jun. 10, 2009, entitled "DEVICE AND METHOD FOR MONITORING OF ABSOLUTE OXYGEN SATURATION AND TOTAL HEMOGLOBIN CONCENTRATION", incorporated herein by reference in it's entirety.

REFERENCE TO RELATED APPLICATIONS

Cross-reference is hereby made to the commonly-assigned related U.S. application Ser. Nos: 12/797,815, 12/797,816 and 12/797,823 all entitled "TISSUE OXYGENATION MONITORING IN HEART FAILURE", to Cinbis et al.; Ser. Nos. 12/797,800 and 12/797,811both entitled "ABSOLUTE CALIBRATED TISSUE OXYGEN SATURATION AND TOTAL HEMOGLOBIN VOLUME FRACTION", to Kuhn et al.; Ser. Nos. 12/797,781 and 12/797,793, both entitled "SHOCK REDUCTION USING ABSOLUTE CALIBRATED TISSUE OXYGEN SATURATION AND TOTAL HEMOGLOBIN VOLUME FRACTION" to Kuhn et al.; Ser. No. 12/797,736, entitled "ACTIVE NOISE CANCELLATION IN AN OPTICAL SENSOR SIGNAL", to Kuhn et al., and Ser. Nos. 12/797,736 and 12/797,770, both entitled "DEVICE AND METHOD FOR MONITORING OF ABSOLUTE OXYGEN SATURATION AND TOTAL HEMOGLOBIN CONCENTRATION" to Kuhn et al., all of which are incorporated herein by reference in their entireties.

TECHNICAL FIELD

The disclosure relates generally to medical devices and, in particular, to a medical device and associated method for monitoring oxygen saturation and total hemoglobin volume fraction.

BACKGROUND

Ambulatory monitoring of blood or tissue oxygen saturation in implantable medical devices is generally limited to monitoring trends of uncalibrated oxygen saturation measurements over relatively short periods of time. The influence of body motion, optical path length, sensor location, and the relationship of an uncalibrated oxygen saturation index to the physiological status of the tissue, e.g. to actual tissue oxygenation, can result in a broad statistical distribution of the response of an uncalibrated oxygen saturation index to patient conditions. Pulse oximeters are used for bedside monitoring of a calibrated measure of hemoglobin oxygen saturation using absorbance measurements of red an infrared light. External, non-invasive devices are available which use fiber optic light sources for monitoring tissue oxygen saturation based on the absorbance of near-infrared light by hemoglobin and myoglobin. However, chronic ambulatory monitoring of tissue oxygen availability in a blood-perfused tissue would be useful for monitoring a patient condition. A need remains for a sensor capable of monitoring calibrated tissue oxygen saturation and total hemoglobin volume fraction that is reduced in size and power requirements for use in an implantable or wearable medical device for ambulatory patient monitoring.

DETAILED DESCRIPTION

Figure 1A:
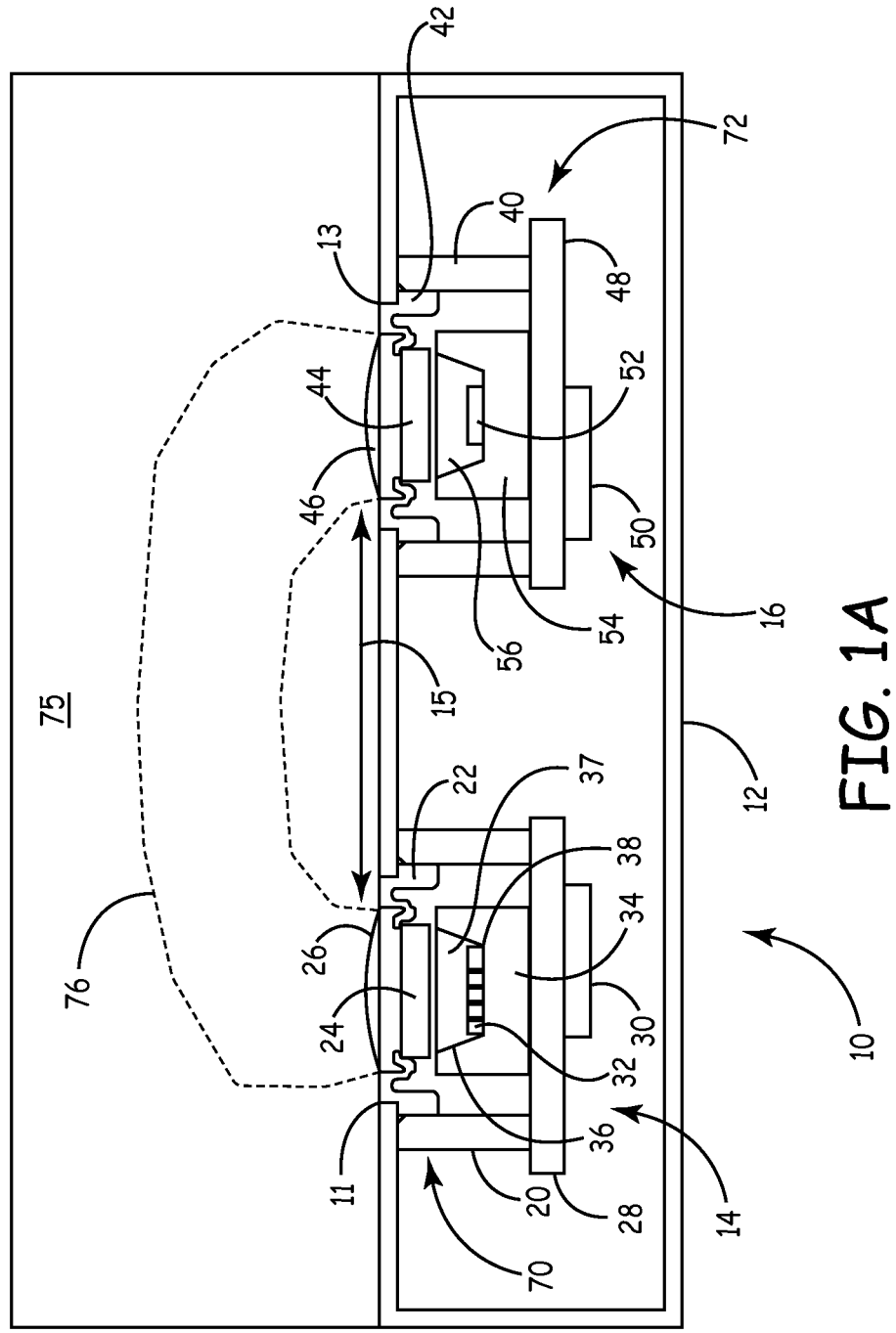
FIG. 1A is a sectional view of an implantable optical sensor configured for monitoring tissue oxygenation.

In the following description, references are made to illustrative embodiments. It is understood that other embodiments may be utilized without departing from the scope of the disclosure. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1A is a sectional view of an implantable optical sensor configured for monitoring tissue oxygenation. The term "tissue oxygenation" as used herein refers to the availability of oxygen to a localized tissue volume and thus refers to the availability of oxygenated hemoglobin. The term "total hemoglobin volume fraction" (HbT) refers to the concentration of red blood cells in a measurement volume carrying hemoglobin and thus relates to the total hemoglobin concentration as a fraction of a measurement volume. Stated differently, the total hemoglobin volume fraction, which can be expressed as a percentage, is the volume percentage of red blood cells carrying oxygenated and deoxygenated hemoglobin in the measurement volume. Thus a measurement of HbT will include contributions from red blood cells present in any arteries, capillaries, and veins which may be present in the measurement volume.

Absolute tissue oxygen saturation ($O_2$Sat) is the portion (or percentage) of the total hemoglobin that is in an oxygenated state. More specifically, $O_2$Sat relates to the available hemoglobin binding sites holding an oxygen molecule. Thus, "tissue oxygenation monitoring" as used herein refers to monitoring both $O_2$Sat (or an index thereof) and HbT (or an index thereof). Tissue oxygenation monitoring may involve determining absolute measurements of $O_2$Sat and HbT or determining trends of these measurements or trends of indices of these measurements. When either $O_2$Sat or HbT are reduced, a blood-perfused tissue can become hypoxic.

$O_2$Sat measurements as described herein refer to the oxygen saturation of the hemoglobin present in the circulating blood in a local tissue. As such, any capillary, arterial and venous blood volume within the optical pathway of the sensor will contribute to the $O_2$Sat measurement. Typically, the sensor will be placed over a uniform, homogenous volume of the blood-perfused tissue so as to measure the $O_2$Sat in the microcirculation of the tissue, with minimal influences from the arterial and venous blood. The measurement of $O_2$Sat in the microcirculation provides a local measurement of tissue oxygen saturation whereas the oxygen saturation of arterial and venous blood will change systemically. The local measurement of $O_2$Sat is correlated to the partial pressure of oxygen measured directly in the tissue.

Sensor 10 shown in FIG. 1A includes a light emitting portion 14 and a light detecting portion 16 configured in a sealed housing 12, which may be hermetically sealed. Housing 12 encloses optical sensor components and optionally other circuitry of an associated medical device. Housing 12 may be a dedicated optical sensor housing or may enclose other device circuitry and components in a multi-function implantable or wearable medical device. For example, housing 12 may enclose circuitry of an implantable pacemaker or cardioverter defibrillator, an implantable or wearable physiological monitor, implantable neurostimulator, implantable fluid pump, or other implantable or wearable medical device. Housing 12 may alternatively correspond to, or be mounted within, an insulative, elongated body of a medical electrical lead.

It is contemplated that sensor 10 can be implemented in association with a medical device that is fully implantable (i.e. no components extending externally from the patient). The wholly implantable medical device may be contained within housing 12 and may have medical electrical leads, catheters or other components extending therefrom. In an alternative embodiment, sensor 12 may be implemented in association with a medical device that is wearable by the patient. The wearable device may be contained within housing 12 which is strapped or adhered to a patient's skin. Housing 12 would enclose circuitry performing the functionality described herein for emitting and detecting light and computing $O_2$Sat and HbT measurements, for use in tissue oxygenation monitoring.

The light emitting portion 14 and the light detecting portion 16 each include a lens 24 and 44, respectively. Lens 24 passes light emitted from the light emitting portion 14 into an adjacent tissue volume 75. Tissue volume 75 encompasses a measurement volume 76 shown schematically in FIG. 1 and representing the volume of tissue falling within an optical path of sensor 10 extending from light emitting portion 14 to light detecting portion 16. Body tissue volume 75 may be any homogenous or heterogenous bodily fluid or tissue, including, but not limited to, blood, skeletal muscle, neural tissue, myocardium, skin, etc. The depth and size of measurement volume 76 within tissue volume 75 will depend on the spacing 15 between the emitting portion 14 and the detecting portion 16, among other factors such as emitting and detecting lens sizes, light source geometry (e.g., area of light sources and proximity to the emitting portion lens), light detector size and geometry (area of light detector and proximity to the detecting portion lens), cavity reflectivity within the sensor and reflectivity of external sensor surfaces.

Light scattered by measurement volume 76 and incident on light detecting portion 16 will be passed by lens 44 into the light detecting portion 16. Lens 24 and lens 44 are commonly formed from sapphire and may be hermetically sealed in openings 11 and 13 formed in housing 12. Lenses 24 and 44 may be sealed within openings 11 and 13, respectively, using ferrules 22 and 42, respectively. Ferrules 22 and 42 are bonded to lenses 24 and 44, e.g. using a gold braze, a polymer adhesive, or other suitable bonding method that provides a hermetic seal between the ferrule material and the lens material and is compatible with other manufacturing processes used in fabricating sensor 10.

Housing 12 may be formed, for example, from titanium, stainless steel, ceramic, glass, or a medical grade polymer. In one embodiment, housing 12 and ferrules 22 and 42 are each formed from titanium. Ferrules 22 and 42 may be welded within openings formed in housing 12 to maintain hermeticity of sensor 10 and an implantable device in which sensor 10 is assembled. The optical window assembly generally disclosed in U.S. Pat. No. 5,902,326 (Lessar, et al.), hereby incorporated herein by reference in its entirety, may be implemented in embodiments of the present disclosure. Lenses 22 and 44 may alternatively be sealed directly to housing 12.

Polymeric seals 26 and 46 may be formed over lenses 24 and 44 and ferrules 22 and 42, respectively. Seals 26 and 46 may be formed, for example, from silicone rubber or another material that is substantially optically transparent to the wavelengths emitted by light emitting portion 14. Seals 26 and 46 protect the bond formed between the ferrules 22 and 42 and the corresponding lens 24 or 44 from the corrosive effects of bodily fluids and provide a smooth surface (which may be convex as shown) that reduces the susceptibility of sensor 10 to blood clot formation and excessive fibrotic tissue encapsulation over lenses 24 and 44. Blood clot formation and fibrotic tissue encapsulation may reduce light transmission into and out of sensor 10. Though not explicitly shown in FIG. 1A, seals 26 and 46 may extend further over ferrules 22 and 42 to cover the bond between the ferrules 22 and 42 and the adjacent housing 12.

The emitting portion 14 includes a light emitting assembly 70 coupled to ferrule 20 (or directly to housing 12). Light emitting assembly 70 includes light sources 32, a circuit board 28, and an optically-insulating wall 20 surrounding light sources 32. Suitable light sources include, without limitation, optoelectronic devices such as light emitting diodes (LEDs), lasers such as vertical cavity surface emitting lasers (VCSELs), luminescent, phosphorescent or incandescent light sources. Light source(s) 32 are mounted on a circuit board 28, which may be a printed circuit board or include wired connections or other integrated circuitry methods, to enable the necessary connections for applying a drive signal, typically a current signal, to each of light sources 32 to cause light emission. Wall 20 surrounds the light sources 32 to prevent scattering of light within housing 12 and promote transmission of light through lens 24 toward adjacent body tissue volume 75.

Wall 20 may be formed from a rigid, light-insulating material, such as a liquid crystal polymer. Alternatively, wall 20 can be formed from other light-insulating materials, for example any polymer material formed as a molded component, and may be non-rigid in some applications. Wall 20 is securely coupled to circuit board 28. Wall 20 may be coupled to circuit board 52 by applying a coating as a hard, die coat dam holding wall 20 to the board 52 as generally described in U.S. patent application Ser. No. 12/116,705, hereby incorporated herein by reference in its entirety.

Light sources 32 each emit light corresponding to spaced-apart wavelengths for use in monitoring absolute tissue oxygen saturation. Emitted light passes through lens 24 and enters body tissue volume 75. One or more light sources may be included in light emitting portion 14. The number of light sources and corresponding light emission wavelengths will be selected according to the requirements of a particular application and will depend on the physiological condition or events that are being.

In one embodiment four LEDs emit light at different individual wavelengths spaced apart between approximately 625 nm and approximately 900 nm. While each light source is referred to herein as emitting an individual wavelength, it is recognized that a light source, such as an LED, may emit a narrow band of wavelengths, typically centered substantially on a specified wavelength.

In one embodiment, and without limitation, light sources 32 emit light in the red to infrared spectrum as indicated by the approximate wavelengths referred to above. It is contemplated, however that other embodiments may include light emission only in the visible spectrum or only in the non-visible spectrum. In one embodiment light is emitted only in the infrared spectrum, e.g. greater than approximately 720 nm, such that no visible light is emitted making light emission by the sensor less perceivable, or unperceivable, to the patient.

Light sources 32 may be mounted in a custom package 34 along a surface elevated from circuit board 28. In the embodiment shown, light sources 32 are mounted along an upper surface 38 of a molded plastic package 34 which includes a lead frame (not shown). Light sources 32 may be embodied as LEDs or other light sources and are mounted in package 34 to protect and facilitate electrical connections between light source dies and circuit board 28. Package 34 may be formed with thermally conductive materials to act as a heat sink for drawing heat away from the light sources 32. Mounting light sources 32 in package 34 may also shorten the distance between light sources 32 and lens 24.

Package 34 may include a recessed cup area 36 in which electrically conductive die pads are positioned for receiving and coupling to the light sources 32. Cup 36 may be filled with an optical coupling material 37 to reduce the reflection of light at material boundaries, for example at the photonic surfaces of light sources 32 or at the inner surface of lens 24. Optical coupling material 37 filling cup 36 reduces the reflection of emitted light at component interfaces within light emitting portion 14. More specifically, material 37 filling cup 36 has a high refractive index for optically coupling light sources 32 with lens 24 in order to reduce the reflection of emitted light as light leaves the photonic surfaces of light sources 32 as compared to light reflected at the photonic surfaces when interfaced with air. Material 37 may also be configured to reduce reflections of emitted light at the inner surface of lens 24 as compared to reflections that would otherwise occur at a lens inner surface-to-air interface. As such, optical coupling material 37 filling cup 36 may be in direct contact with the lower surface of lens 24 and/or in direct contact with the photonic surfaces of light sources 32.

The detecting portion 16 includes a light detecting assembly 72 coupled to ferrule 42 (or directly to housing 12). Assembly 72 includes a light detector 52, also referred to herein as a "photodetector", circuit board 48, and an optically insulating wall 40 surrounding light detector 52. Wall 40 may have an exterior hard die coating for retaining wall 40 against circuit board 48. The light detector 52 may be embodied as a photodiode. Other components suitable for use as a light detector include a photoresistor, phototransistor, photovoltaic cell, photomultiplier tube, bolometer, charge-coupled device (CCD) or an LED reverse-biased to function as a photodiode. Light detector 52 may be provided in a custom or commercially available package 54 including a lead frame and mounted on circuit board 48 to enable appropriate electrical connections between circuitry 50 and photodetector 52.

Wall 40 surrounds the photodetector 52 to promote light traveling through lens 44 to fall on photodetector 52 and minimize stray light within housing 12 from reaching photodetector 52. Package 54, when included, promotes reflection of light onto photodetector 52, in which case wall 40 primarily acts to minimize stray light within sensor 10. Wall 40 may share a common side with wall 20 in some embodiments, and may be formed from rigid, opaque or light-insulating material, such as a liquid crystal polymer. Alternatively, wall 40 can be formed from other, light insulating materials, for example any polymer material formed as a molded component, and may be non-rigid in some applications. Wall 40 may be attached to printed circuit board 48 using a coating applied as a hard, die coat dam holding wall 40 to the board 48.

In some embodiments, an electrically insulative material may fill open spaces between packages 34 and 54 and the respective ferrules 22, 42 and housing 12 to prevent electrical coupling between components mounted in packages 34 and 54 and ferrules 22, 42 and housing 12. When housing 12 serves as an active electrode, for example, when housing 12 forms the housing of an implantable cardioverter defibrillator, a minimum spacing may be required between the housing 12 and the light sources 32 and light detector 52.

While separate circuit boards 28 and 48 are shown, it is contemplated that a single circuit board may be provided with both the light emitting assembly 70 and the light detecting assembly 72 mounted thereon. The single circuit board or the separate circuit boards 28 and 48 may additionally include circuitry corresponding to other functions of an implantable medical device in which sensor 10 is incorporated.

Integrated circuitry 30 included on circuit board 28 is electrically coupled to light sources 32 to deliver drive signals to activate light sources 32 to emit light. Integrated circuitry 50 included on circuit board 48 is coupled to photodetector 52 to receive the electrical signal emitted by photodetector 52 in response to scattered light incident on photodetector 52. Circuitry 50 provides a signal to processing circuitry which may be housed within housing 12 or otherwise included in an associated medical device. Processing circuitry, as will be described herein, may be included on circuit board 48 or implemented separately and is configured to compute $O_2Sat$ and Hbt using the photodetector output signal and perform a monitoring algorithm, e.g. for monitoring oxygenation of tissue volume 75. Integrated circuitry 50 may include an analog-to-digital converter and memory for digitizing the analog output signal from photodetector 52, providing the digitized signal to the processing circuitry, storing measurement results for future retrieval as well as storing calibration coefficients. In other embodiments, only raw signals are collected and stored, then transmitted to a processor, which may be included in an implantable or wearable device or located in an external device such as a programmer or computer, where the raw data is processed to determine calibrated $O_2Sat$ and Hbt values.

In some embodiments, sensor 10 additionally includes a reference photodetector 38 in light emitting portion 14. The light entering tissue volume 75 from emitting portion 14 may change over time during chronic use of sensor 10 due, for example, to drift in the photonic output of light sources 32 and/or changes in the optical properties of seal 26. Relative changes in oxygen saturation over relatively short periods of time, for example seconds, minutes, hours or perhaps even days, will not be significantly affected by drift of the light source output or fouling of the seal 26. Changes in the intensity of the emitted light due to such causes will be gradual and may only occur over a period of months or years. Such changes will thus have a substantially equal effect on both an initial measurement and a subsequent measurement used to compute a relative oxygen saturation change over relatively shorter durations of time such as seconds, minutes, hours, or days. In contrast, an absolute, calibrated measurement of tissue oxygen saturation may become erroneous over time if the relative intensity of the emitted light for each light source changes over time without compensation.

Control circuitry 30 may include circuitry for receiving an output signal from reference photodetector 38 for detecting changes in the intensity of the light emitted by emitting portion 14 over time for use in computing or adjusting $O_2Sat$ and HbT and/or for use in controlling light emission as will be further described below. In some embodiments, the computation of absolute tissue oxygen saturation using an output signal from photodetector 52 also requires a measurement of the light intensity emitted by emitting portion 14 (which can be measured by reference photodetector 38) in order to compute the attenuation of light at predetermined wavelengths. In other embodiments, adjustments of calculated tissue $O_2Sat$ are made based on changes in the intensity of light emitted by emitting portion 14 since an initial emitted light intensity measurement was made.

When multiple light sources 32 are included for emitting light at separate spaced apart wavelengths, light emitting portion 14 may include a light diffusing material to diffuse the light emitted by each light source before it enters tissue 75. Diffusion of separately emitted wavelengths before entering tissue 75 will promote similar optical pathways of the separate wavelengths through tissue 75. A light diffusing material may be an epoxy filled with glass beads to promote light scattering. A light diffusing material may be included in the material filling cup 36, coated over the top surface of package 34, or coated on an inner or outer surface of lens 24.

Figure 1B:
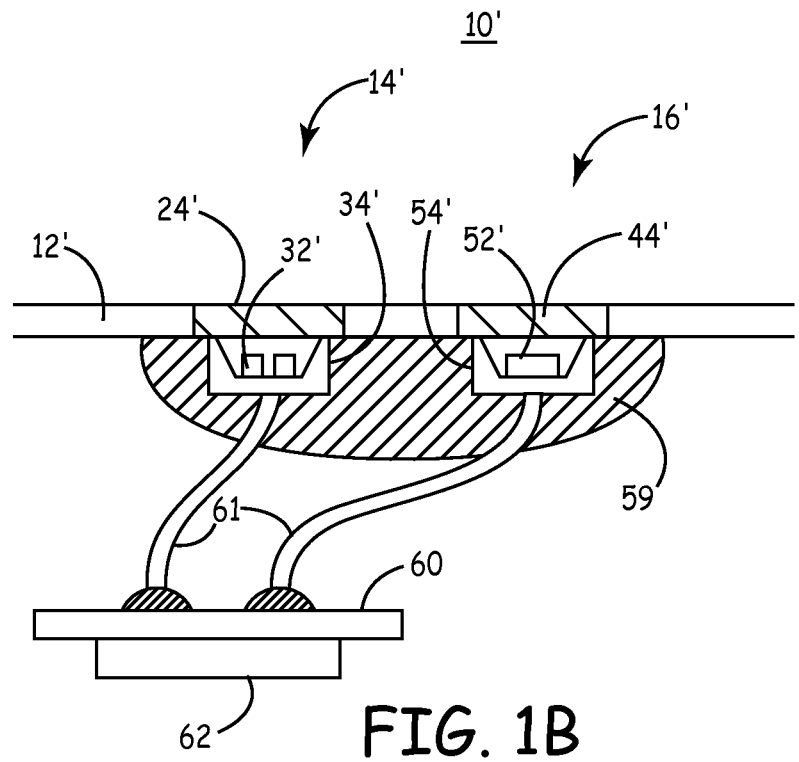
FIG. 1B is a side sectional view of an alternative embodiment of an optical sensor for use in an implantable or wearable medical device.

FIG. 1B is a side sectional view of an alternative embodiment of an optical sensor 10' for use in an implantable or wearable medical device. Sensor 10' includes an emitting portion 14' and a detecting portion 16' housed in a hermetically sealed housing 12'. Housing 12' includes openings in which lenses 24' and 44' are sealed, for example using epoxy or other sealing adhesive. A light emitting package 34', including one or more light sources 32', is mounted directly to an inner surface of lens 24'. A light detecting package 54', including a light detector 52', is mounted directly to an inner surface of lens 44'. An epoxy or other adhesive that is optically transparent at the wavelengths of interest may be used to mount packages 34' and 54' directly to respective lenses 24' and 44'.

Conductors 61, which may be laser ribbon bonds, wires, flexible circuits, or the like, electrically couple the light emitting package 34' and the light detecting package 54' to circuitry 62 mounted on circuit board 60. As described previously, circuitry 62 includes circuitry for providing drive signals to light sources 32' in light emitting portion 14' and for receiving the output signal from light detecting portion 16'.

A black polymer 59 is dispensed over the back side of packages 34' and 54' to prevent stray light within housing 12', provide optical insulation of the light detector 52', and add mechanical stability to the light emitting and light detecting portions 14' and 16'.

Figure 1C:
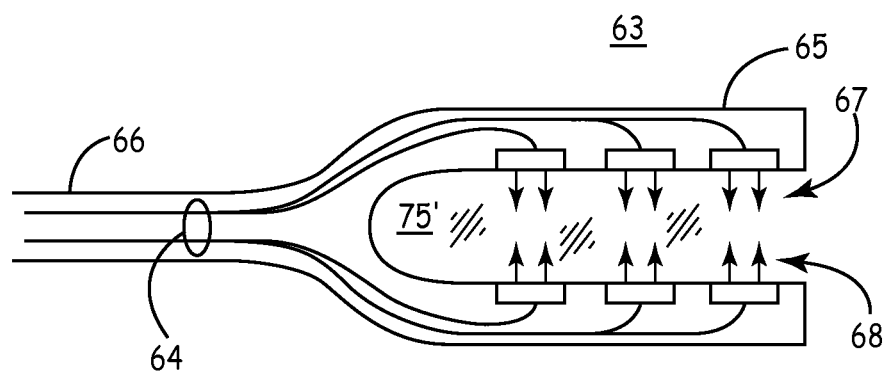
FIG. 1C is a side sectional view of an alternative embodiment of an optical sensor for ambulatory patient monitoring.

FIG. 1C is a side sectional view of an alternative embodiment of an optical sensor 63 for ambulatory patient monitoring. One or more light emitting portions 67 and one or more light detecting portions 68 are assembled along opposing inner surfaces of a generally "C"-shaped or clamshell style cuff 65. Cuff 65 may extend from a distal end of an elongated lead 66. Conductors 64 may extend from each of the light emitting portions 67 and light detecting portions 68 to be electrically coupled to a lead connector at a proximal lead end for electrical connection to an associated medical device.

Alternatively, cuff 65 may be a leadless device. Cuff 65 may house functional circuitry (as generally described below) needed for sensor 63 to operate a wireless device.

Cuff 65 may be provided as a flexible device, for example fabricated from a flexible polyurethane or silicone material. Alternatively cuff 65 may be fabricated from a rigid material that rigidly maintains opposing alignment of an emitting portion 67 with a detecting portion 68. Cuff 65 may be formed as a single, continuous piece as shown in FIG. 1C including one or more emitting and detecting portions 67 and 68 in facing opposition along a housing. Alternatively, cuff 65 may include two separate, sealed housings, one for housing the emitting portions 67 and another separate housing for the detecting portions 68. Cuff 65 may then include a rigid or flexible C-shaped connector extending between the two separate housings to form the generally C-shaped cuff 65.

Cuff 65 may be provided in varying sizes to allow sensor 63 to be placed around a body tissue 75' of interest, which may be, for example, a blood vessel, a skeletal muscle, a digit, the thenar muscle in the palm of the hand, or a rib and adjacent intercostal muscle tissue. By positioning emitting and detecting portions 67 and 68 spaced apart and in facing opposition to each other, light emitted by an emitting portion 67 and transmitted through tissue 75' is received by light detecting portion 68. The measurement volume will be defined by an optical pathway that is approximately linear through the tissue 75' that is "sandwiched" between the emitting and detecting portions 67 and 68. Shifts in the opposing alignment of an emitting portion 67 and a detecting portion 68 may be tolerated since absolute $O_2Sat$ measurements described herein are relatively independent of the volume of tissue in the optical pathway of the sensor (when the tissue is a uniform, homogenous tissue). If shifting does occur, resulting in measurements through an undesired optical pathway in non-uniform or non-homogenous tissue or produces erroneous measurements of the tissue oxygenation, the inclusion of multiple emitting and detecting portions 67 and 68 allows an optimal emitting portion and detecting portion pair to be selected for achieving an optimal output signal.

Figure 1D:
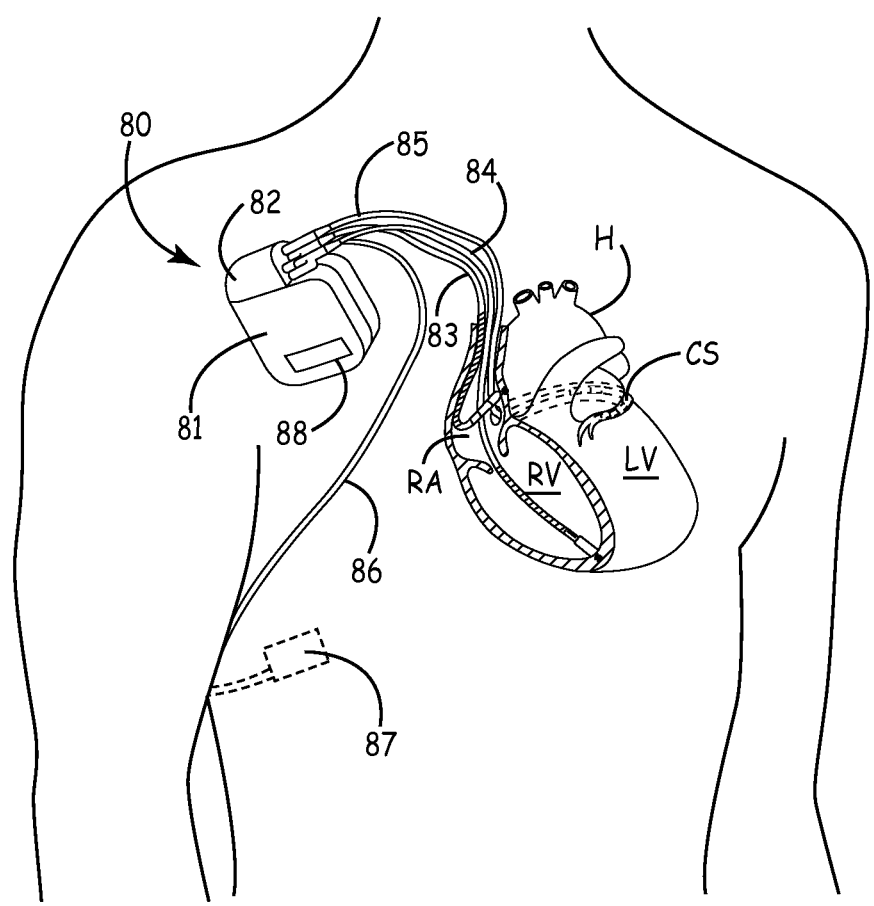
FIG. 1D is a schematic drawing of an implantable medical device (IMD) configured for both monitoring the function of and delivering therapy.

FIG. 1D is a schematic drawing of an implantable medical device (IMD) 80 configured for both monitoring the function of and delivering therapy to heart H. In FIG. 1, heart H is shown in a partially cutaway view illustrating right atrium RA, right ventricle RV, left ventricle LV, and coronary sinus CS.

IMD 80 is shown embodied as an ICD that includes a pulse generator for delivering electrical stimulation to heart H for use in cardiac pacing therapies, cardioversion and/or defibrillation. Another example of an implantable medical device in which methods described herein may be practiced would be a subcutaneous cardioverter/defibrillator having electrodes implanted subcutaneously rather than transvenously as described herein.

IMD 80 includes hermetically-sealed housing 81, connector block assembly 82, right atrial (RA) lead 83, right ventricular (RV) lead 84, left ventricular (LV) lead 85, and optical sensor lead 86. IMD 80 further includes circuitry and a power source, which are located within housing 81, for controlling the operation of IMD 80. The circuitry communicates with leads 83-86 through electrical connectors within connector block assembly 82. A can electrode is formed on or is a part of the outer surface of housing 81, and may act as an electrode in a unipolar combination with one or more of the electrodes carried by leads 83-85. Leads 83-85 extend from connector block assembly 82 to right atrium RA, right ventricle RV, and coronary sinus CS adjacent left ventricle LV, respectively, of heart H. Leads 83-85 each carry one or more electrodes for sensing EGM signals attendant to the depolarization and repolarization of heart H, for providing pacing pulses for causing depolarization of cardiac tissue in the vicinity of the distal ends thereof, and for providing cardioversion/defibrillation shocks. When provided, a shock is typically delivered between a combination of electrodes carried on RA and RV leads 83 and 84 and the can electrode.

IMD 80 may include an optical sensor 88 along the housing 81 for emitting light into a tissue volume adjacent IMD 80 and detecting light scattered by the tissue volume for measuring light attenuation by the tissue. The measured light attenuation is used to compute tissue oxygenation measurements as will be described herein.

Alternatively or additionally, an optical sensor 87 may be carried by a lead 86 extending from IMD 80. Lead 86 extends from connector block assembly 82 to optical sensor 87, which is extravascularly-implanted, typically subcutaneously or submuscularly, at a desired tissue site. In other embodiments, sensor 87 may be carried by a lead and placed transvenously or transarterially in the blood stream itself. A lead-based sensor may be positioned to transmit light outward through the wall of a vessel to monitor perfusion in adjacent tissue.

Sensor 87 may alternatively be embodied as a wireless sensor, implanted remotely from IMD 80 or worn externally by the patient. Sensor 87 provided as a wireless sensor includes telemetry circuitry for wireless telemetric communication with IMD 80.

Figure 2A:
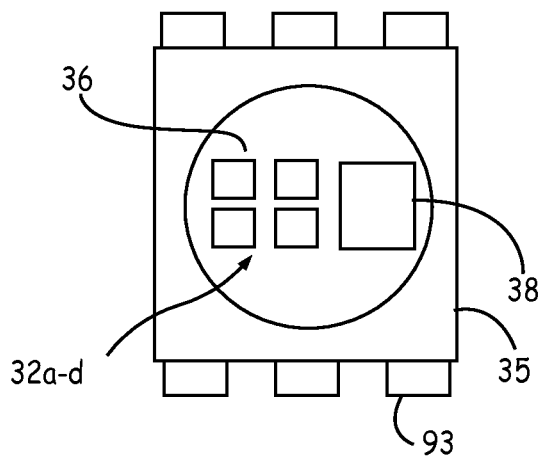
FIG. 2A is a top view of an assembly that may be used in light emitting portion of FIG. 1A-D.

FIG. 2A is a top view of light source package 34 that may be used in the light emitting portions of the sensors shown in FIGS. 1A-1D. Package 34 includes a plastic molded substrate 35 including a lead frame having multiple exposed electrodes 93. Package 34 includes recessed cup portion 36 having die pads (not explicitly shown in FIG. 2A) to which light sources 32a-d (also referred to collectively as 32) and photodetector 38 are mounted and electrically coupled. Package 34 facilitates connection of light sources 32 to drive circuitry located on a circuit board via respective leads of the lead frame extending within substrate 35 to individual exposed electrodes 93. Similarly, reference photodetector 38 is electrically coupled via a respective electrode 93 to output circuitry located on a circuit board for providing a reference light signal corresponding to the intensity of light emission by light sources 32.

Package 34 optionally includes a heat sink material that absorbs heat produced by light sources 32. Package 34 may be mounted on a circuit board 28 as shown in FIG. 1 such that electrodes 93 are electrically coupled to control circuitry 30 (FIG. 1) included on a circuit board 28, e.g. by printed or wired connections. Alternatively, package 34 is mounted directly to a lens inner surface as shown in FIG. 1B and is electrically coupled by conductors extending to a circuit board.

In one embodiment, the four light sources 32a-d are selected to emit light in the red to infrared spectrum. In one embodiment one light source 32a is selected to emit red light at a wavelength of approximately 660 nm to approximately 680 nm. Another light source 32d is selected to emit infrared light at a wavelength of approximately 800 to approximately 890 nm. The remaining two light sources 32b and 32c are selected to emit red or infrared light at wavelengths that are intermediate the wavelengths of light sources 32a and 32d. For example, light source 32b is selected to emit light at a wavelength of approximately 720 nm, and the other light source 32c is selected to emit light at a wavelength of approximately 760 nm. In one embodiment, 40 nm spacing of the wavelengths is selected, e.g., 680 nm, 720 nm, 760 nm, and 800 nm, though other wavelength spacings could be used. Wavelength spacings may be selected to maximize the sensitivity of sensor output signals to $O_2$Sat and HbT. Wavelengths may be equally or unequally spaced.

Reference photodetector 38 is provided to measure the intensity of light emitted by light emitting portion 14. In one embodiment, photodetector 38 is exposed to lens 24 as shown in FIG. 1 such that light detected by photodetector 38 includes light emitted by light sources 32a-d and light remitted (i.e., scattered) by adjacent tissue and incident on the emitting portion 14 and passing back through lens 24. In this configuration, an intensity input measurement by reference photodetector 38 will include effects of drift or other changes in light source output as well as effects of fouling of seal 26 or other changes in the optical properties of sensor 10 which may affect the intensity of light emitted from emitting portion 14 and entering tissue volume 75.

Figure 2B:
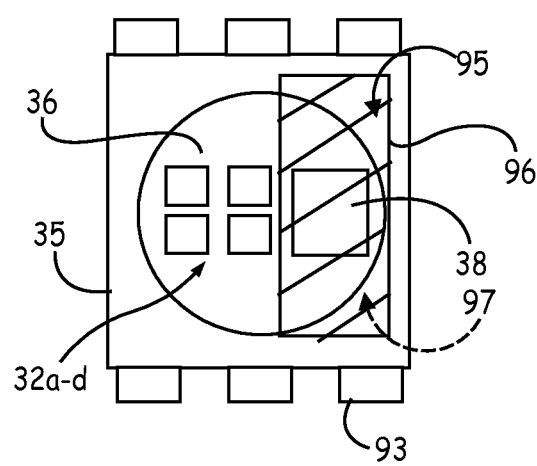
FIG. 2B is a top view of an alternative embodiment of an assembly for use in light emitting portion of FIG. 1A-D.

FIG. 2B is a top view of an alternative embodiment of a light source package 34" for use in light emitting portion 14 of FIG. 1A. Identical components in assembly 34" are identified by the same reference numerals as in package 34 of FIG. 2A. In package 34", an optical shield 96 is positioned to minimize the remitted light that passes through lens 24 into emitting portion 14 from directly reaching photodetector 38. Optical shield 96 may be formed as a coating on an inner or outer surface of lens 24 (shown in FIG. 1), or over the top surface of package 34". Optical shield 96 may alternatively be formed as a separate component that is positioned between lens 24 and package 34", over photodetector 38. An inner surface 97 of shield 96 that faces photodetector 38 may be provided as a substantially flat surface 97 or as curved surface to direct light from light sources 32 onto photodetector 38.

Shield 96 may be reflective or absorptive and may have different properties on an outer surface 95 facing toward tissue 75 than on its inner surface 97 facing toward photodetector 38. For example, shield 96 may be diffuse reflective or absorptive on the inner surface 97 facing photodetector 38, but may be reflective on the outer surface 95 facing tissue 75 so as to promote propagation of secondary reflections into tissue 75.

In this embodiment, reference photodetector 38 provides an output signal corresponding to the light intensity emitted by light sources 32a-d that is more strongly dependent on the intensity of light emitted by light sources 32 and relatively less dependent on remitted light entering light emitting portion 14. In this way, the output signal of reference photodetector 38 is less influenced by changes in emitted light intensity that occur as the result of fouling of seal 26 or other material factors that may attenuate the light emitted by light sources 32a-d before it enters an adjacent tissue. Reference photodetector 38 may be used to monitor the performance of light sources 32 and provide a feedback signal for controlling the drive signals applied to light sources 32. The reference signal may be used in computing absolute oxygen saturation, to control light source drive signals, and/or adjust computed oxygen saturation measurements.

Figure 2C:
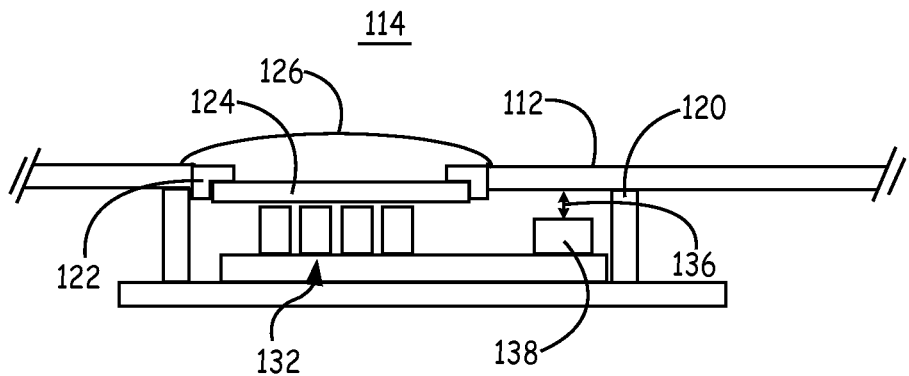
FIG. 2C is a side view of an alternative embodiment of a light emitting portion.

FIG. 2C is a side view of an alternative embodiment of a light emitting portion 114. In this embodiment, the ferrule 122 and opening in housing 112 are sized such that lens 124 and seal 126 are positioned over light sources 132. Reference photodetector 138 is positioned within housing 112 and insulating wall 120 away from lens 124 such that photodetector 138 is not directly beneath any portion of lens 124. Reference photodetector 138 is positioned directly beneath a portion of housing 112 and/or ferrule 122 such that photodetector 138 is not directly exposed to light scattered back into light emitting portion 114 through lens 124. It is recognized that some portion of remitted light scattered or reflected within wall 120 may fall upon photodetector 138. However, photodetector 138 is expected to provide an output signal that is more strongly dependent on the intensity of light emitted by light sources 132 and relatively less dependent on remitted light entering light emitting portion 114 through lens 124.

By selecting a distance 136 between photodetector 138 and housing 112, and/or selecting the optical properties of the surfaces within emitting portion 114, for example along inner surfaces of housing 112 and/or wall 120, the proportion of emitted light reaching photodetector 138 from light sources 132 and the proportion of remitted light reaching photodetector 138 from adjacent tissue through lens 124 may be selectively controlled to improve the sensitivity of the photodetector output signal to light source emission. As described in conjunction with FIG. 2B, this reference photodetector 138 provides a reference signal that may be used to monitor and control light source 132 performance. The reference signal may be used in computing absolute oxygen saturation, to control light source drive signals, and/or adjust computed oxygen saturation measurements.

Figure 3:
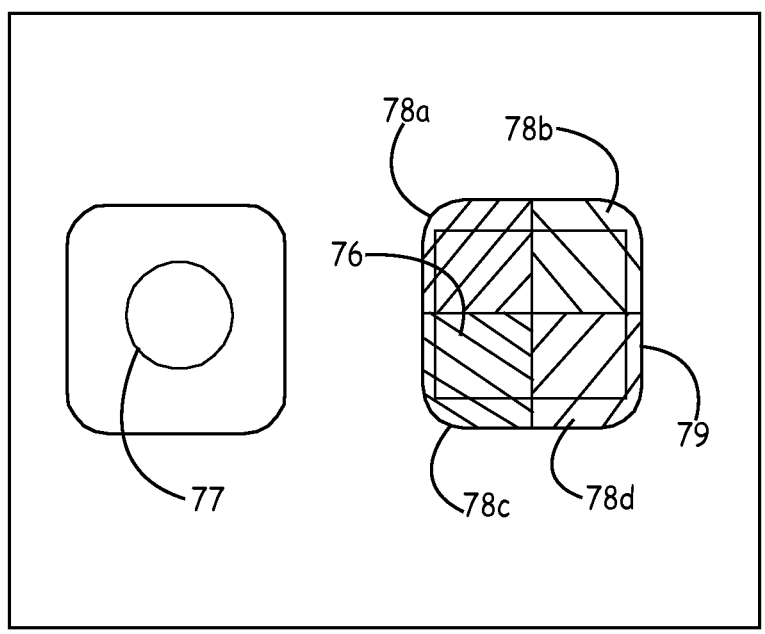
FIG. 3 is a top schematic view of an optical sensor according to another embodiment.

FIG. 3 is a top schematic view of an optical sensor 75 according to another embodiment. A photodetector 76 is positioned beneath lens 79 in a light detecting portion. Lens 79 includes four different filters 78a through 78d. Filters 78a-d may be embodied as four different coatings applied to lens 44 each selected to pass a desired wavelength of remitted light. In other embodiments, filters 78a-d may include a thermally or electrically-actuated filter mechanism, such as a rotating wheel, or a tunable filter such as an etalon. Sensor 75 may include a white light source 77 in the emitting portion, or multiple light sources, such as LEDs, emitting separate wavelengths concurrently. Remitted light passing through lens 79 will include a spectrum of light wavelengths encompassing at least four wavelengths for which attenuation measurements will be made.

Filters 78a-d enable photodetector 76 to produce an output signal including components of the remitted light corresponding to each of the four wavelengths filtered by filters 78a-d. In alternative embodiments, multiple photodetectors may be provided in the light detecting portion. Each photodetector may receive scattered light via a respective light filter and produce an output signal corresponding to a particular wavelength or narrow wavelength band. Alternatively, each photodetector may be provided as a reverse biased LED to function as a narrow-band photodiode as generally described in U.S. patent application Ser. No. 11/955,025, hereby incorporated herein by reference in its entirety.

Figure 4:
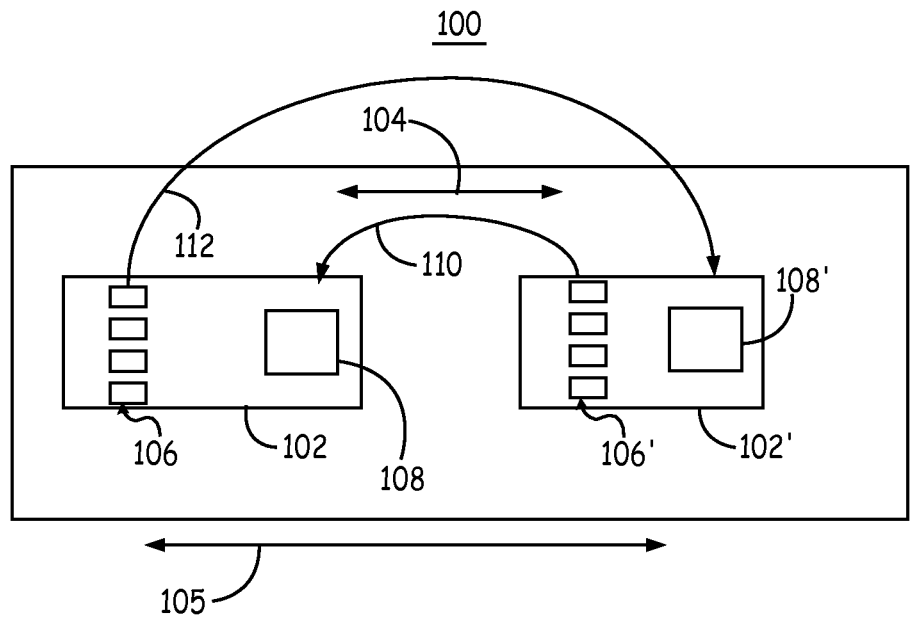
FIG. 4 is a top schematic view of a sensor according to yet another embodiment.

FIG. 4 is a top schematic view of a sensor 100 according to another embodiment. Sensor 100 includes two modular assemblies 102 and 102' each manufactured to have identical light emitting and light detecting components. Specifically, assemblies 102 and 102' each include light sources 106 and 106' respectively and light detectors 108 and 108', respectively. The functionality of each assembly 102 and 102' is selectable such that one assembly 102 or 102' is selected to operate as an emitting portion and the other assembly 102 or 102' is selected to operate as a detecting portion. This functional selection may be made at the time of manufacture and not alterable thereafter. Alternatively, this selection may be dynamic under the control of control circuitry included in the associated medical device. Functional selection of assemblies 102 and 102' may be based on user input or in response to feedback or self-diagnostic measurements made by sensor 100.

By arranging the light sources 106 and 106' and the light detectors 108 and 108' in a particular spatial manner with respect to one another, two different optical pathways 110 and 112, and thus two different measurement volumes, may be realized depending on the selection of the functionality of each assembly 102 and 102'. In the example configuration shown, the assemblies 102 and 102' are positioned next to each other such that the photodetector 108 of portion 102 is nearest the light sources 106' of assembly 102'. Likewise, the light sources 106 of assembly 102 are farthest from the photodetector 108' of assembly 102'. If assembly 102 is selected as the detecting portion and assembly 102' is selected as the emitting portion, the emitting-to-detecting spacing 104 is relatively shorter than a spacing 105 that would result if functional selection of assemblies 102 and 102' were reversed (i.e., assembly 102 selected as emitting and assembly 102' selected as detecting). The longer emitting-to-detecting spacing 105 will result in a relatively longer (and deeper) optical pathway 112 (shown schematically) when assembly 102 is emitting light than the optical pathway 110 (shown schematically) that results when assembly 102' is emitting light.

As such, through proper orientation of assemblies 102 and 102' and the emitting and detecting components therein, different optical pathways may be selected through the selectable functionality of the assemblies 102 and 102'. While a single configuration is shown in FIG. 4, it is recognized that numerous arrangements of two or more assemblies 102 and 102' and the emitting and detecting components therein may be conceived to allow multiple light emitting and light detecting combinations to be selected, each combination corresponding to a different optical pathway through a tissue volume. The different optical pathways may differ in location along the tissue and/or may differ in length (depth) within the tissue.

When one modular assembly, e.g. assembly 102, is selected as the emitting portion, the photodetector 108 in the emitting portion assembly 102 may operate to provide a reference signal corresponding to emitted light intensity. Alternatively, the photodetector 108 in assembly 102 selected to operate as an emitting portion may be functionally disabled during light emission. The light sources 106' in the other module 102' selected to operate as a light detecting portion in this example will be inactive during light detection by photodetector 108'.

In other embodiments, assembly 102 selected as the emitting portion may include light detection by photodetector 108 to yield measurements at a very shallow tissue depth. A partial mask between the photodetector 108 and light sources 106 may be used to prevent photodetector saturation but allow some direct shunting of emitted light to photodetector 108 to detect drift of the photonic output of light sources 106. Shallow measurements may be useful to indicate a thickness of a fibrous encapsulation of the sensor. A photodetector 108 included in an assembly 102 may serve the dual purpose of light detector for light sources 106' in another assembly 102' and providing a reference measurement of emitted light intensity for assembly 102.

By including modular assemblies 102 and 102' that can function as either emitting or detecting portions, the functionality of each assembly can be switched if a light source or a light detector in one assembly fails. The functionality may also be switched during tissue oxygenation monitoring to obtain measurements at different tissue depths and volumes. Measurements at different tissue depths can provide a measure of tissue uniformity, as will be further described herein. Briefly, an $O_2$Sat measurement using optical pathway 110 may be compared to an $O_2$Sat measurement using optical pathway 112. Similarity between the two measurements indicates tissue uniformity since the $O_2$Sat measurements computed as generally described herein are independent of the measurement volume defined by the optical pathway of the sensor in a uniform, homogenous tissue. A significant difference between the two measurements indicates tissue heterogeneity or non-uniformity (oxygenation gradient through the tissue). Based on measurement comparisons, one optical pathway 110 or 112 may be more desirable for use in monitoring tissue oxygenation. For example, one pathway 112 may penetrate through an adjacent tissue volume and reflect off of bone, other device components, or enter other undesired tissue. Comparisons of oxygenation measurements obtained using different optical pathways may be used in selecting the functionality of the assemblies 102 and 102'.

Measurements at different tissue depths or along different pathways may also provide measurement redundancy to promote confidence in $O_2$Sat and HbT measurements. Manufacturing of identical modular assemblies can simplify manufacturing processes and potentially reduce costs.

In FIG. 4, the light sources 106 are arranged linearly such that each individual light source is approximately the same distance 105 from photodetector 108. Differential spacing between each light source 106 and photodetector 108 may have significant effects on $O_2$Sat and HbT measurements due to differing optical path length for each light source and differing tissue properties within each optical path of the separate wavelengths when the adjacent tissue volume is non-uniform or heterogeneous. The magnitude of the effects of different optical path length and tissue heterogeneity or oxygenation gradients may be minimized by minimizing the differential spacing between separate light sources 106 and photodetector 108. Spatial arrangements of light sources 106 relative to photodetector 108 that remove or minimize any differential spacing are desirable. When the overall distance 105 between light sources 106 and photodetector 108 is relatively large compared to spacing between individual light sources 106 and the resulting differential spacing to photodetector 108, the effects of differential spacing of light sources 106 to photodetector 108 is reduced. For example, when distance 105 is approximately 20 times greater (or more) than the spacing between light sources 106, measurement error due to differences in optical path length between individual light sources 106 and photodetector 108 may be insignificant. Likewise, if the overall distance 105 is large compared to the characteristic size of tissue structures that introduce heterogeneity in the tissue, the effects of different optical pathways (having different optical properties) through the tissue for each individual light source will be reduced. As such, to minimize measurement error, it is desirable to place the optical sensor over substantially homogeneous tissue, maximize the distance 105 between light sources 106 and photodetector 108, and minimize the differential distances between individual light sources and photodetector 108.

Furthermore, assembly 102 (and 102') may include a light diffusing material as described previously to diffuse separately emitted light wavelengths and thereby reduce the effects of differential spacing between individual light sources 106 and photodetector 108. The size of the window in the housing and the associated lens may also be minimized to reduce any differences in optical pathways between individual light sources 106 and photodetector 108. For example, if the light sources are grouped in a square of four as shown in FIGS. 2A and 2B, an opening in the housing and the associated lens over the grouped light sources may be centered on the square grouping with a diameter no greater than the square to create a point of light emission that is similar for the separate light wavelengths.

An optimal distance 105, which is also referred to herein as the "emitting-to-detecting spacing", for a particular sensing application will be dependent on a number of factors. For implantable or wearable devices, it is generally desirable to minimize the distance 105 to reduce the overall device size and power requirements. However, reduced emitting-to-detecting spacing can increase measurement error as described above and will limit the depth of the optical pathway within the adjacent tissue volume. As such, multiple design considerations will be taken into account when selecting the emitting-to-detecting spacing 105 for a particular monitoring application. As an example an emitting-to-detecting spacing 105 may be anywhere between approximately 5 mm and approximately 25 mm, however embodiments described herein are not limited to any particular emitting-to-detecting spacing.

Figure 5:
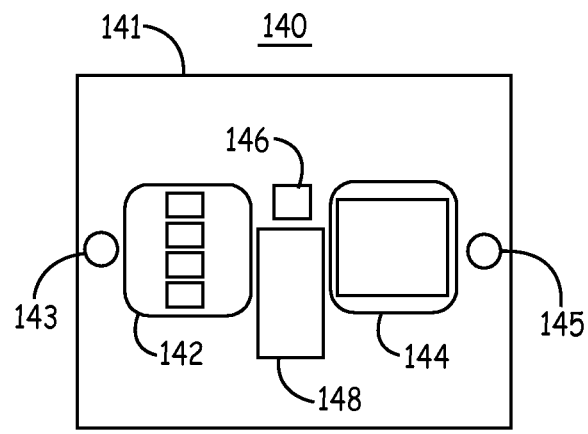
FIG. 5 is a top view of a sensor for monitoring tissue oxygenation according to another alternative embodiment.

FIG. 5 is a top view of a sensor for monitoring tissue oxygenation according to an alternative embodiment. Sensor 140 includes light emitting portion 142 and light detecting portion 144, which may correspond to any of the light emitting and light detecting portions described above. Sensor 140 additionally includes a temperature sensor 146. Temperature sensor 146 may utilize a thermistor, a thermocouple, a P-N diode, a junction of a bipolar junction transistor (BJT) device, or other temperature sensitive device such as the absolute temperature sensing circuit generally described in U.S. Pat. No. 6,682,135 (Davis, et al.), hereby incorporated herein by reference in its entirety. Temperature sensor 146 is provided to account for changes in tissue oxygenation caused by changes in temperature. Temperature data may be used in discriminating between possible causes of tissue oxygenation changes. Temperature monitoring can be used to remove, adjust or otherwise correct for the influence of temperature on tissue oxygenation measurements.

In one embodiment, sensor 140 includes a heating element 148. While heating element 148 is shown schematically in FIG. 5 as being confined to a specific area of sensor housing 141, it is recognized that heating element 148 may be incorporated over a larger area of sensor 140 and/or an associated medical device to allow uniform tissue heating and may be implemented using multiple discrete elements spaced apart to promote even tissue heating across a desired surface area of the tissue. Heating element 148 may be a resistor or other element that can be controlled to produce heat without causing undue overheating of the adjacent tissue or harming electronics within sensor 140 or an associated medical device.

Heating element 148 may be mounted on an outer or inner surface of the housing 141 of sensor 140 and may be backed by a thermally insulative material to prevent heating of other components within sensor 140.

Controlled heating of the adjacent tissue may be used in a number of ways during tissue oxygenation monitoring. In one embodiment, heating element 148 may be used to heat the adjacent tissue volume to a predetermined temperature whenever tissue oxygenation measurements are acquired to provide temperature-controlled measurements thereby reducing the variability of oxygenation measurements that may be caused by temperature variation. Temperature sensor 146 may be used to verify when the adjacent tissue temperature has reached a desired temperature to enable oxygenation measurements and prevent tissue overheating.

In other embodiments, tissue heating may be applied to cause vasodilation which will raise the arterial contribution to the local tissue oxygenation measurements. Depending on the placement of sensor 140, tissue oxygenation measurements will generally include a contribution from capillary blood volume and may include a contribution from venous blood volume and arterial blood volume. For monitoring oxygenation in a tissue such as skeletal muscle, it is generally desirable to avoid a large contribution from arterial or venous blood volume. The oxygen saturation and total hemoglobin in the capillaries are expected to best reflect the availability of oxygen to the local tissue. However, arterial oxygen saturation monitoring may be desirable in some applications to provide a systemic measurement of $O_2Sat$. By heating the tissue locally to cause arterial dilation, a measured absolute $O_2Sat$ may approach arterial blood oxygen saturation and therefore be used to monitor arterial oxygen, even when sensor 75 is not placed directly against an artery. The arterial oxygen saturation measurement (at an increased temperature to cause vasodilation) and local tissue oxygenation measurements (at an intrinsic tissue temperature) may be used alone or in combination to detect and discriminate patient conditions.

In some embodiments, multiple measurements of tissue oxygenation may be obtained as the local tissue temperature is adjusted incrementally to different levels under the control of heating element 148 and temperature sensor 146. Such measurements may allow for observation of normal or abnormal tissue oxygenation response to temperature change.

It is recognized that the incorporation of heating element 148 is not limited to embodiments including a temperature sensor 146 and vice versa. A heating element 148 may be included that reliably produces a controlled amount of heat in a repeatable manner such that temperature sensing is not required for controlling and monitoring tissue heating. Likewise, temperature monitoring by sensor 146 may be used without artificially altering the intrinsic tissue temperature using heating element 148.

While not explicitly shown in FIG. 5, heating element 148 and temperature sensor 146 will be electrically coupled to control and output circuitry included in housing 141 to allow control of heating element 148 and to receive and process temperature sensor signals.

In some embodiments, optical sensor 140 includes electrodes 143 and 145 along sensor housing 141 to provide electrical stimulation of excitable tissue adjacent to sensor 140. Electrical stimulation of adjacent tissue will increase the tissue metabolic demand for oxygen. The availability of oxygen to the local tissue before, during and/or after electrical stimulation may be monitored by measuring oxygen saturation and total hemoglobin volume fraction using optical sensor 140.

Figure 6:
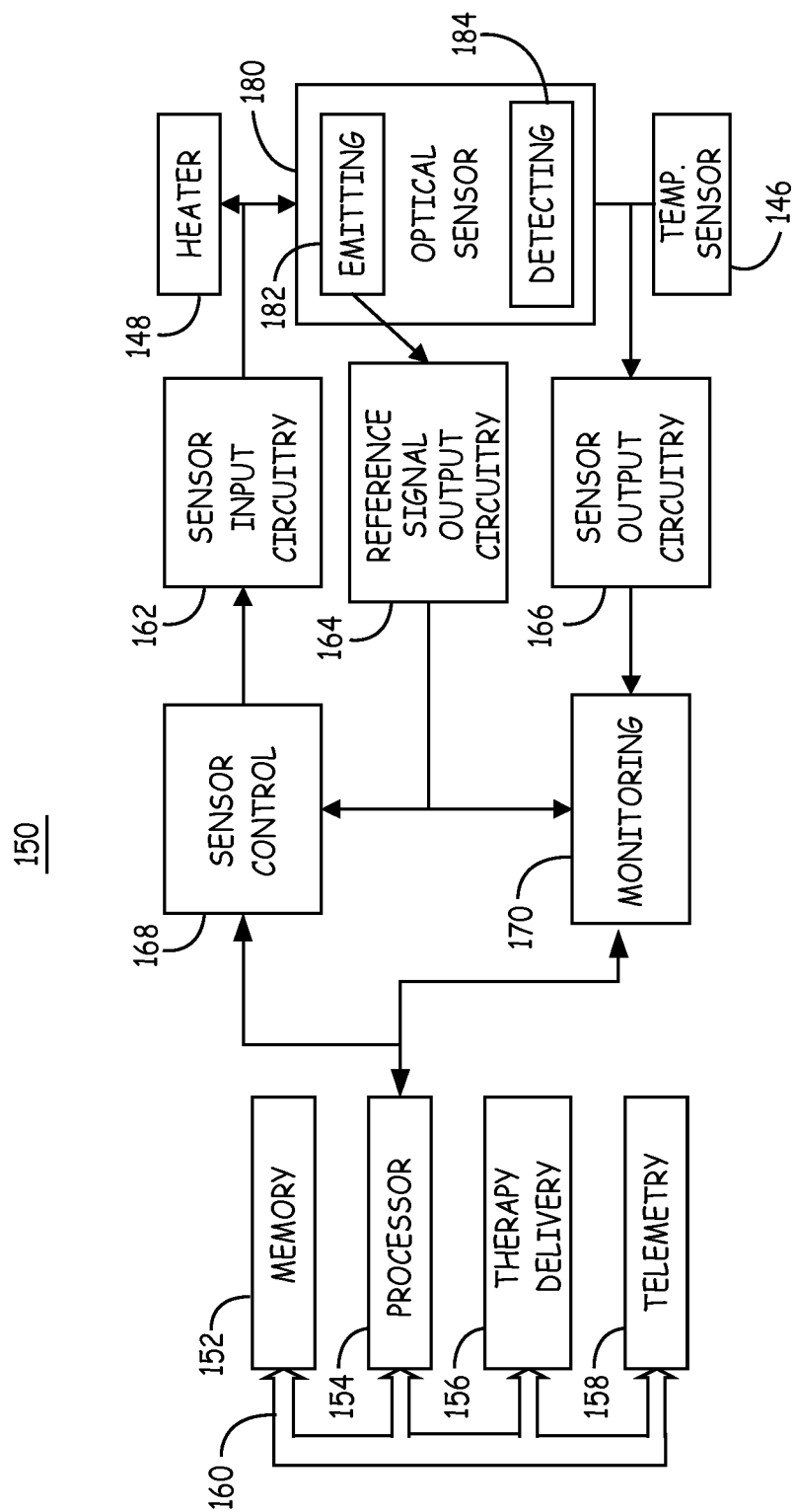
FIG. 6 is a functional block diagram of a medical device associated with an optical sensor for monitoring oxygen saturation and total hemoglobin.

Changes in the availability of oxygen with changes in metabolic demand may be evaluated. Electrodes 143 and 145 are electrically coupled to pulse generation circuitry (not shown) within housing 141 and the application of stimulation pulses would be controlled by sensor control circuitry. FIG. 6 is a functional block diagram of an implantable medical device 150 associated with an optical sensor for monitoring $O_2Sat$ and HbT. Device 150 includes an optical sensor 180, which may correspond to sensor 10 of FIG. 1 or any of the other sensor embodiments described herein. Device 150 further includes sensor input circuitry 162, sensor output circuitry 166, and optional reference signal output circuitry 164 if a reference photodetector is included in light emitting portion 182 of the optical sensor 180. Sensor input circuitry 162, which may correspond to circuit 30 of FIG. 1A, is coupled to a light emitting portion 182 of sensor 180. Sensor input circuitry 162 provides input signals to the optical sensor 180. In particular, sensor input circuitry 162 provides the drive signals applied to light sources in light emitting portion 182 to cause controlled light emission.

Sensor input circuitry 162 is controlled by sensor control module 168 which coordinates the time, duration, and frequency of drive signals produced by sensor input circuitry 162. A period of no light emission may be included to allow ambient light measurement. In one embodiment, the drive signals are applied sequentially to cause sequential (i.e., non-simultaneous) light emission at separate spaced-apart wavelengths by individual light sources. In this way, the detecting portion 184 will receive scattered light at an individual wavelength during any given interval of active light emission by sensor 180. It is recognized that referring to an "individual" wavelength can include a narrow bandwidth of wavelengths approximately centered on a specified wavelength emitted by the light source. The sequential emission of light wavelengths, referred to herein as "time multiplexing", allows multiple, separate light signals to be acquired and processed. A single $O_2Sat$ and HbT measurement will require some minimum interval of time to perform which corresponds to the cumulative time durations of each of the separately emitted wavelength signals.

In alternative embodiments, the sensor input circuitry 162 is controlled by sensor control module 168 to deliver drive signals simultaneously to each of the light sources. Simultaneous emission of spaced-apart wavelengths by multiple light sources may be used when wavelength filtering is applied by the detecting portion 184. Alternatively, simultaneous emission of multiple, spaced-apart wavelengths may be controlled to emit each of the wavelengths at separate, unique frequencies. Each light source will emit light having a signature frequency fluctuation and is referred to herein as "frequency multiplexing". The detecting portion 184 will receive scattered light at all of the wavelengths simultaneously with each wavelength modulated to a signature frequency. The photodetector signal is then demodulated to obtain the individual wavelength signals.

Simultaneous emission with filtering or frequency multiplexing methods of controlling light emission allows simultaneous light emission and detection of all wavelengths of interest. Changes in light attenuation due to oxygen and hemoglobin changes in the tissue volume can be measured simultaneously for all of the wavelengths rather than at discrete time intervals for separately emitted wavelengths. This allows for a more instantaneous measurement of $O_2Sat$ and HbT as compared to the time-multiplexed method of controlling light emission.

The different wavelengths may be modulated at frequencies that are much greater than the frequency of ambient light changes. Demodulation of the detected light signal will reduce or eliminate effects of ambient light since the low frequency components of the detected light signal corresponding to ambient light changes will be substantially removed from the demodulated photodetector output signal.

Sensor output circuitry 166 receives the photodetector signal from detecting portion 184 and demodulates and digitizes the signal to provide a digital signal to monitoring module 170. Monitoring module 170 uses the optical signal to compute an absolute $O_2$Sat and a HbT. The absolute $O_2$Sat is provided to a processor 154 (or other control circuitry) for detection of a physiological condition, determining a need for delivering or adjusting a therapy, and/or monitoring effectiveness of a delivered therapy.

It is recognized that IMD 150 may include other sensors for sensing physiological signals such as intracardiac EGM or ECG signals, blood pressure, patient activity, patient posture, or the like. Such sensor signals may be used in combination with the monitored absolute tissue oxygen saturation and total hemoglobin volume fraction for determining when a therapy is needed and delivered by therapy delivery module 156. Therapy delivery module 156 may include electrical pulse generation capabilities for delivering cardiac pacing, cardioversion or defibrillation or nerve stimulation. Therapy delivery module 156 may additionally or alternatively include a fluid delivery pump for delivering a pharmaceutical or biological fluid to the patient.

Data acquired by processor 154 relating to $O_2$Sat and HbT measurements may be stored in memory 152 and/or transferred to a medical device programmer, home monitor, computer, or other external or bedside medical device via telemetry module 158 for review by a clinician. Processor 154 transmits data to and from memory 152, therapy delivery module 156, and telemetry module 158 via data/address bus 160.

In embodiments including a reference photodetector in the emitting portion 182, reference signal output circuitry 164 provides an output signal to sensor control 168 and/or to monitoring module 170. In one embodiment, the reference signal output circuitry provides an emitted light intensity feedback signal to sensor control 168 in a feedback control loop to maintain emitted light at a desired intensity. Each light source drive signal is automatically adjusted to maintain the emitted light at a desired intensity (or within a desired range). In this way, the emitted light spectra is reliably maintained over time promoting the accuracy of $O_2$Sat and HbT measurements computed using initial calibration constants and assuming stable light emission intensity. Accordingly, sensor control 168 may include comparators and other logic circuitry for determining if a reference emitted light intensity signal is within a target range. If not within the desired range, the drive signal is adjusted by sensor control 168, e.g., in an iterative manner, until the target range is reached.

In an alternative embodiment, the reference emitted light intensity signal provided by circuitry 164 is received by monitoring module 170. Monitoring module 170 may use the emitted light intensity and a detected light intensity to compute light attenuation at each wavelength. The attenuation at each wavelength is used to compute second derivative attenuation spectra as will be described in greater detail below for computing $O_2$Sat and HbT.

Alternatively, monitoring module 170 uses changes in the emitted light intensity to adjust a computed absolute $O_2$Sat value. Absolute tissue $O_2$Sat may be computed assuming a constant emitted light intensity. The measured emitted light intensity may be used to adjust a computed $O_2$Sat. For example, an initially measured emitted signal intensity and a currently measured emitted signal intensity (for one or all light sources) can be used to adjust or correct an absolute tissue $O_2$Sat computed using only the detected light signal and calibration constants.

As described above in conjunction with FIG. 5, a heating element 148 may be included in sensor 180, or more generally in or coupled to device 150, to operate in conjunction with sensor 180 for tissue oxygenation monitoring. Heating element 148 is coupled to sensor input circuitry 162 which provides operating signals, under the control of sensor control 168, to heating element 148 to cause controlled heating of tissue adjacent to sensor 180.

A temperature sensor 146 may also be included in device 150 to allow local temperature monitoring in the vicinity of sensor 180. Temperature sensor 146 is coupled to sensor output circuitry 166 to provide a temperature signal to monitoring module 170. The influence of changes in local tissue temperature may then be taken into account in monitoring tissue oxygenation measurements.

Figure 7:
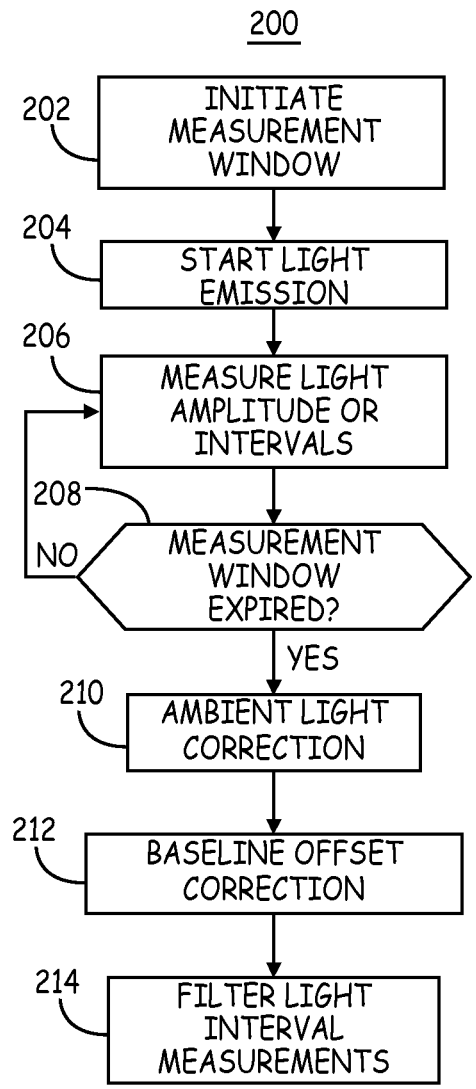
FIG. 7 is a flow chart of one method for operating an optical sensor for monitoring tissue oxygenation in an implantable or wearable medical device.

FIG. 7 is a flow chart 200 of one method for operating an optical sensor for monitoring tissue oxygenation in an implantable or wearable medical device. Flow chart 200 is intended to illustrate the functional operation of the device, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the device. Providing software to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202, a measurement time window is initiated. In various applications, tissue oxygenation monitoring may be continuous, periodic, or triggered in response to other events monitored by the medical device. In the example shown in method 200, the monitoring is performed during a periodic or triggered measurement window. After initiating the measurement window, light emission is started at block 204. Light emission at selected wavelengths may be controlled in a simultaneous, time multiplexed or frequency multiplexed manner or provided as pulsed or continuous white light.

At block 206, the electrical output signal generated by the photodetector is measured. The output signal may be analyzed using an amplitude approach or an integration approach. In the integration approach, an integrator is included in the sensor output circuitry for integrating the photodetector signal, for example using a capacitor. The signal may be integrated over fixed time intervals, which may be on the order of 0.10 to 100 ms for example. The magnitude of the integrated signal at the end of the fixed time interval is stored as a sample data point and corresponds to scattered light received by the light detecting portion of the optical sensor during the fixed time interval.

Alternatively, the photodetector signal may be integrated until a predetermined integrated signal magnitude is reached and the time interval required to reach the predetermined magnitude is stored as a sample data point. When the integration approach is used to obtain sample data points, the fixed integration time interval or the predetermined integrated signal magnitude may be selected to allow the signal values to be acquired at or above the frequency of a physiological condition of interest.

In other embodiments, the amplitude of the photodetector signal may be analyzed directly by sampling the signal throughout the measurement window. Such sampling may correspond to sequential time intervals of light source activation times during time multiplexed light source operation. Alternatively the frequency may be selected to be greater than the greatest frequency modulation of a light source in the emitting portion to allow sampling all wavelengths of emitted light in a frequency multiplexed algorithm.

The measurement window may be set to allow time to acquire a desired number of output signal sample points for each of the desired wavelengths. The photodetector signal amplitude or integrated signal amplitude or time interval continues to be sampled during the measurement window until it expires as determined at decision step 208.

After acquiring the desired number of samples, the drive signals controlling the light emitting portion may be turned off and the sampled data points may be stored and processed for computing $O_2$ Sat and HbT as will be described further below. The sampled data points may be filtered or averaged at block 214 to provide smoothing of signal data or removal of artifact.

At blocks 210 and 212 corrections of sample data may be made to reduce the influence of ambient light and baseline offset. Corrections performed in blocks 210 and 212 may be executed before or after filtering at block 214. Ambient light may be measured directly by measuring the optical signal when the light emitting portion of the optical sensor is not emitting light. The ambient light contribution may then be subtracted from the light signal. Baseline offset (sometimes referred to as the "dark signal" or "dark interval") is caused by current leakage within the optical sensor electronics that occurs in the absence of light. Correction for the baseline offset for a given sensor can be made based on a dark signal or dark interval for that sensor, measured, for example, at the time of device manufacture and qualification testing. If the baseline offset exceeds a desired threshold, offset correction may be included at block 212 to subtract the offset from the incoming signal data. Corrections made at block 210 and 212 may correspond to light signal corrections generally described in U.S. patent application Ser. No. 12/039,242, hereby incorporated herein by reference in its entirety.

Figure 8:
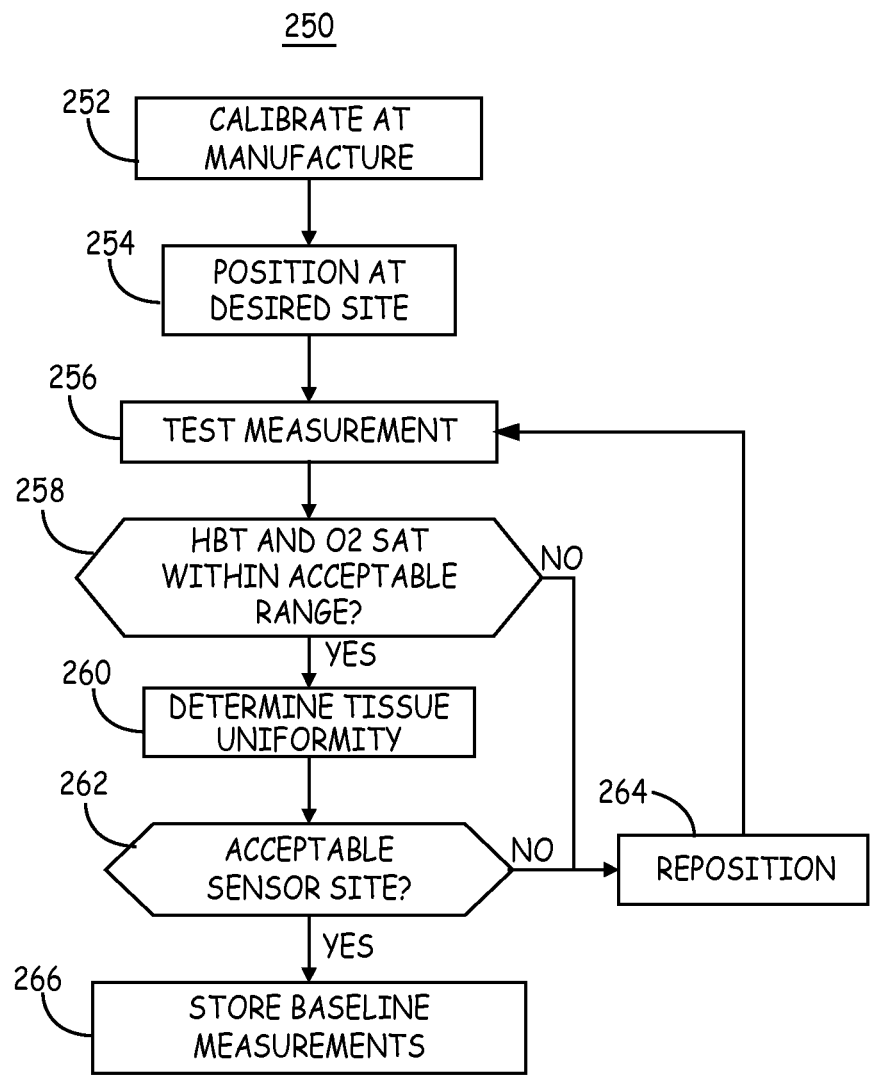
FIG. 8 is a flow chart of a method for using an implantable or wearable medical device including an optical sensor.

FIG. 8 is a flow chart of a method for using an implantable or wearable medical device including an optical sensor. At block 252 of method 250, the optical sensor is calibrated using control samples, for example in an in vitro blood circuit, having known oxygen saturation and total hemoglobin concentration. The calibration method may be used to generate a look-up table. A look-up table of values relating light measurements computed from the photodetector output signal and the known $O_2$Sat and HbT may be stored in the device memory. The look-up table can then be used to derive absolute $O_2$Sat and Hbt values from an optical sensor measurement.

Alternatively, calibration methods may include curve-fitting methods to solve for coefficients defining best-fit curves to the calibration data. In one embodiment, the absolute tissue $O_2$Sat is defined by:

$$O_2\text{Sat} = Ae^{B(SD''(\lambda))} + C \qquad [1]$$

wherein SD" is a scaled second derivative of the attenuation spectra at a selected wavelength $\lambda$. As will be further described below, a scaled second derivative of the attenuation spectra at a selected wavelength is determined by the monitoring module using the photodetector signal. The scaled second derivative is the ratio of the second derivative with respect to wavelength of the attenuation spectra at the selected wavelength $\lambda$ to the second derivative of the attenuation spectra at another wavelength. By properly selecting the wavelength $\lambda$ and the other wavelength used for scaling, the scaled second derivative is an oxygen-dependent and measurement volume-independent ratio. The coefficients A, B and C are determined through best-fit analysis of measurements of the scaled second derivative for calibration samples having known oxygen saturation.

As used herein, a "volume-independent" measure of oxygen saturation refers to a measurement that is substantially independent of the size of the optical sensor path that encompasses a measurement volume within a substantially uniform tissue. In other words, in a uniform, homogenous tissue, a longer optical pathway that encompasses a larger measurement volume and a relatively shorter optical pathway that encompasses a smaller measurement volume within the same uniform tissue will produce substantially equal $O_2$Sat measurements. A volume-dependent measure of oxygen saturation would be dependent on oxygen and the measurement volume and would thus produce two different measurements for two different measurement volumes in the same uniform, homogenous tissue. The second derivative method for computing $O_2$Sat as described herein eliminates scattering effects of a changing measurement volume and provides a volume-independent measurement of $O_2$Sat.

A homogenous tissue is a tissue that includes structures that are relatively small compared to the measurement volume. For example, if measurement volume is related to emitting-to-detecting spacing, a homogenous tissue might be a tissue wherein tissue structures or features have a dimension of approximately 1/10 of the emitting-to-detecting spacing or less. A uniform tissue is a tissue that has uniform oxygenation through the depth of the measurement volume in contrast to an oxygenation gradient. If a tissue is non-uniform or non-homogeneous, different oxygen saturation measurements will be obtained depending on the optical path of the sensor through the tissue.

The total tissue hemoglobin volume fraction can be defined by the equation:

$$\text{HbT} = [M(100 - O_2\text{Sat})^N + L] * [(D''(A)_{\lambda,i}/d\lambda)/SF] \qquad [2]$$

wherein M, N, and L are coefficients determined during calibration and $D''(A)_{\lambda,i}/d\lambda$ is the second derivative of the attenuation spectra with respect to wavelength at a selected intermediate wavelength $\lambda i$. The second derivative of the attenuation spectra with respect to wavelength at a given wavelength is also referred to herein as $D''(\lambda)$. $D''(\lambda)$ is measured for samples containing known total hemoglobin volume fraction and known oxygen saturation. The calibration coefficients M, N and L may then be computed for a best-fit of the measured second derivative values and known $O_2$ Sat and HbT. Alternatively, the measured second derivative values and known $O_2$Sat and HbT may be used to generate a look-up table for converting the measured second derivative values to HbT and $O_2$Sat values.

SF is a spacing factor which may be used to adjust for an emitting-to-detecting portion spacing that may be different during patient monitoring than the spacing used during calibration. Since the HbT measurement is dependent on both oxygen and measurement volume, and measurement volume is dependent on the optical pathway defined at least in part by the spacing between the emitting and detection portions, the HbT measurement needs to be corrected for changes in emitting-to-detecting portion spacing. For example, the sensor may be calibrated using a nominal emitting portion to detecting portion spacing, however when emitting and/or detecting portions are selectable in a sensor or combination of sensors, the spacing used during patient monitoring may be different than that used during calibration. As such, a spacing factor corresponding to selectable emitting and detecting portion spacings may be stored and used to correct the HbT measurement when a different spacing is used during monitoring than during calibration.

At block 254, the sensor is positioned at a desired implant site (or external site in the case of an external device to be worn by the patient). A test measurement is performed at block 256. The absolute $O_2$Sat and HbT are determined from the sensor output signal using the stored calibration data. The measured values are compared to an acceptable measurement range at block 258. This comparison may be performed manually or automatically using a programmed range stored in the medical device memory.

If the $O_2$Sat exceeds a predefined expected range, for example greater than approximately 90%, the sensor may be in a position resulting in arterial blood strongly contributing to the $O_2$Sat measurement. If the monitoring application is concerned with measuring tissue oxygenation rather than arterial oxygen saturation, the sensor may be repositioned at block 264.

Likewise, if the $O_2$Sat is too low, for example less than approximately 80%, the sensor may be in a position resulting in venous blood strongly contributing to the $O_2$Sat measurement. If the absolute $O_2$Sat falls below an expected physiological range for the particular sensing application, the sensor may be repositioned at block 264.

If the HbT is less than a predetermined range, for example less than approximately 1%, the sensor may be improperly positioned against the tissue (poor tissue contact) or positioned over a non-tissue medium or low or non-perfused tissue. For example, if the sensor is positioned over fat, scar tissue, clear body fluids, or other implanted medical device components, HbT may be below a normal physiological range for perfused tissue. HbT greater than an acceptable physiological range, for example greater than approximately 25% for blood-perfused tissue, may indicate blood pooling in the measurement volume beneath the sensor or other sensor measurement error. If the HbT test measurement is outside a predefined acceptable range, the sensor may be repositioned at block 264.

Once the $O_2$Sat and HbT measurements are confirmed to be in an acceptable physiological range at block 258, a tissue uniformity index may be determined at block 260. A tissue uniformity index is determined by utilizing at least two different emitting-to-detecting portion spacings. Accordingly at least two different combinations of light emitting and light detecting portions at two different spacings must be available, on the same or different optical sensors, positioned adjacent a target tissue volume. When at least two different spacings are available, the $O_2$Sat is measured using the two different spacings and compared. A tissue uniformity index may be computed based on the difference between these two measurements, which would involve two different measurement volumes defined by two different optical pathways. For example, a relatively greater emitting-to-detecting portion spacing would result in greater depth of the optical pathway.

If the difference between the two measurements is small, the tissue is relatively uniform and homogenous. If the difference between the two measurements is large, the tissue is non-uniform and/or heterogeneous. A threshold for detecting uniform/homogenous versus non-uniform/heterogeneous tissue volumes may be selected according to a particular application. Detection of heterogenous tissue may warrant repositioning of the sensor. A tissue uniformity index may indicate the most appropriate emitting-to-detecting spacing for measuring within a desired tissue volume. The initial $O_2$Sat, HbT and tissue uniformity measurements can therefore be used to decide if the sensor position is acceptable at block 262. If not, the sensor may be repositioned at block 264.

If acceptable, the sensor is fixed at the desired site, and baseline $O_2$Sat and HbT measurements may be acquired and stored at block 266 according to the needs of the particular monitoring application. Baseline measurements may be acquired for comparison to future measurements, for use in learning algorithms performed during clinical interventions or naturally occurring pathological events, for use in setting thresholds for detecting physiological events, or for initiating continuous monitoring of $O_2$Sat and HbT, i.e. tissue oxygenation.

Figure 9:
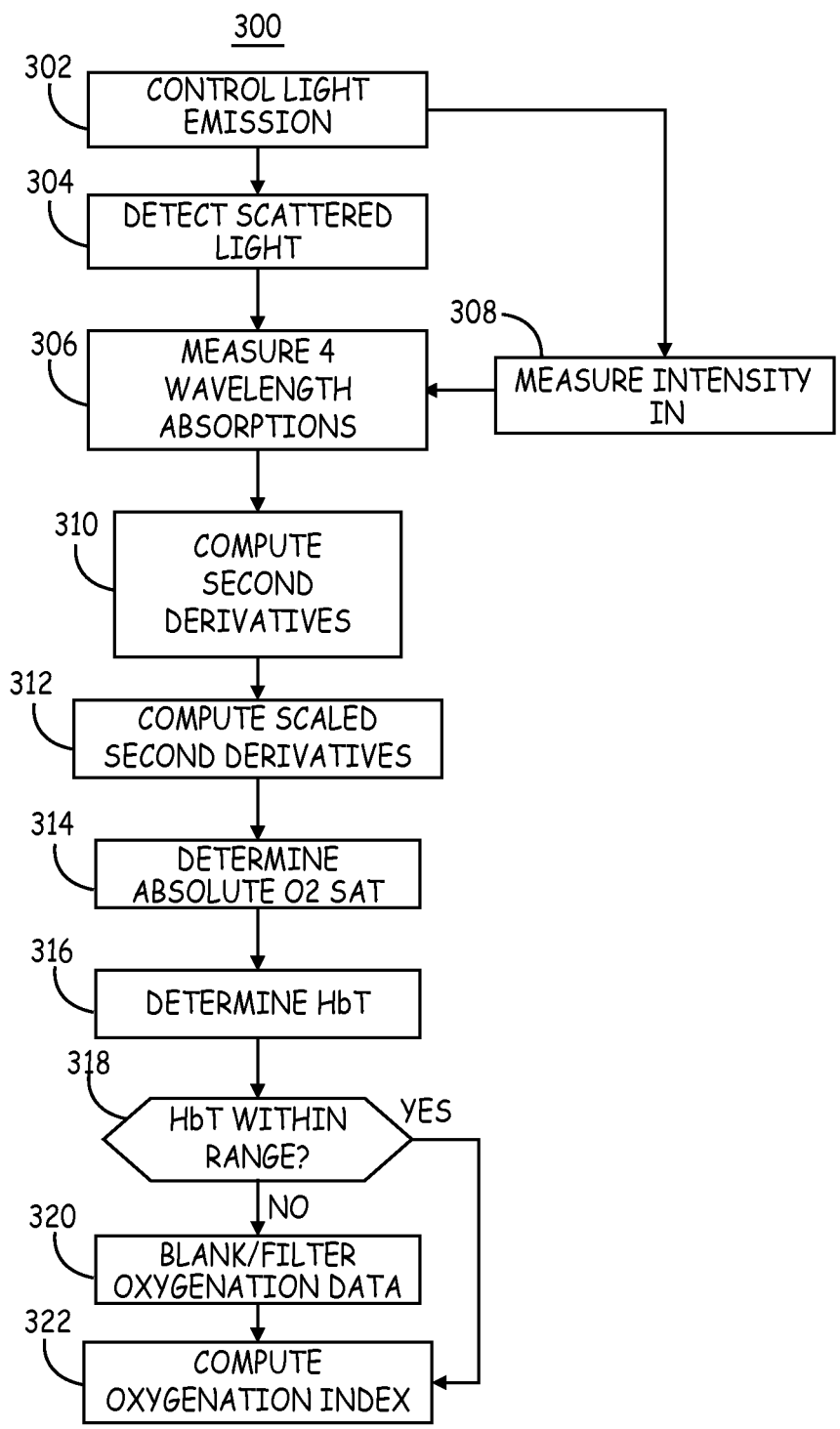
FIG. 9 is a flow chart of a method for operating an optical sensor for monitoring tissue oxygenation.

FIG. 9 is a flow chart of a method 300 for operating an optical sensor for monitoring tissue oxygenation. At block 302, the light emitting portion of the sensor is controlled to emit light by applying drive signals to light sources. As described previously, light sources may be controlled to emit light at different wavelengths in a sequential, time-multiplexed manner, in a simultaneous frequency-multiplexed manner, or simultaneously at multiple wavelengths when filtered in the detecting portion. Light emission may also be provided by a white light source.

A reference photodetector included in the light emitting portion provides an output signal for measuring the intensity of light emitted by the sensor at block 308. The reference photodetector signal is demodulated or otherwise processed to provide an intensity of light emitted for each of the selected wavelengths at which attenuation will be measured.

At block 304, the emitted light scattered by the tissue volume is detected by the photodetector in the light detecting portion. The detecting portion provides an output signal corresponding to the intensity of light received. The output signal is demodulated or otherwise processed to provide an intensity of light received for each of the selected wavelengths.

At block 306, the attenuation spectra is measured. In one embodiment, the attenuation of four wavelengths in the red to infrared spectrum is measured. The attenuation of the four different wavelengths may be measured using sequential detection of the different wavelengths by the photodetector when a time multiplexed light emission control algorithm is used. Alternatively, measurement of the four different wavelengths may involve demodulation or filtering of simultaneously detected light at the four different wavelengths when a frequency multiplexed or simultaneous light emission control algorithm is used. In other embodiments, remitted light from a white light source may be filtered to obtain the four different wavelength attenuation signals. In still other embodiments, light sources configured for narrow-band light detection may be used to detect the four separate wavelengths. The attenuation (A) for a given wavelength (λ) can be measured as the negative logarithm of the ratio of the emitted light intensity ($i_{in}$) to the remitted light intensity ($i_{out}$):

$$A(\lambda) = -\log(i_{in}/i_{out})_{80}$$

[3]

wherein $i_{in}$ can be measured using a reference photodetector in the light emitting portion of the sensor and $i_{out}$ is measured using the output signal of the light detecting portion for a given wavelength. The term "attenuation" measurement as used herein generally refers to a measure of the attenuation of light due to absorption and scattering by tissue along the optical path of the sensor. The measured attenuation may therefore not be an exact measurement of the actual light absorption by the tissue volume since light reflections and scattering can cause attenuation of the remitted light intensity not attributed to actual light absorption by the tissue.

In some embodiments, the emitted intensity $i_{in}$ for each wavelength is measured prior to implantation, e.g., at the time of manufacture, and assumed to be sufficiently stable throughout the usable life of the sensor as to not cause significant measurement error. In this case, a reference photodetector may be eliminated from the light emitting portion of the sensor and thereby reduce overall size and complexity of the sensor. One method for measuring the emitted intensity prior to implantation uses the light detecting portion to measure the remitted light when the sensor is positioned within a calibrated reflective housing. The construction of the emitting portion is designed to minimize or prevent drift in the emitted light intensity over time. Design considerations include minimizing the distance between the tissue and the photonic surfaces of the light sources.

In some embodiments, the output signal intensity for each wavelength may be normalized by a selected output signal intensity. Such normalization will cancel for uniform gain of the output signal. Uniform gain (which may be positive or negative) may result from known or unknown factors, such as motion resulting in a different optical sensor measurement volume within a heterogenous tissue, drift in a light detector amplifier, or partial blockage of the light detector window.

The attenuation for at least four wavelengths is measured to allow the second derivative with respect to wavelength of the attenuation spectra to be determined at two intermediate wavelengths. This determination of second derivatives at two intermediate wavelengths allows for computation of a scaled second derivative. At block 310, the attenuation measurements for each the four detected wavelengths are used to compute a second derivative ($D''(\lambda)$) of an intermediate wavelength $\lambda$, expressed generally as:

$$D''(\lambda) = \frac{\left\{\left(\frac{A(\lambda_{i+1})-}{A(\lambda_i)}\right) \Big/ \left(\frac{\lambda_{i+1}-}{\lambda_i}\right)\right\} - \left\{\left(\frac{A(\lambda_i)-}{A(\lambda_{i-1})}\right) \Big/ \left(\frac{\lambda_i-}{\lambda_{i-1}}\right)\right\}}{[(\lambda_{i+1}-\lambda_{i-1})/2]} \quad (4)$$

wherein $A(\lambda_i)$ is the light attenuation, measured according to Equation 3 above, at the wavelength for which the second derivative is being computed, $A(\lambda_{i+1})$ is the attenuation at the next higher wavelength and $A(\lambda_{i-1})$ is the attenuation at the next lower wavelength of the four wavelengths.

When the wavelength spacing between $\lambda_i$ and neighboring wavelengths is equal, the denominators in the above Equation 4 may be dropped resulting in a simplified equation:

$$D''(\lambda_i) = A(\lambda_{i+1}) - 2A(\lambda_i) + A(\lambda_{i-1}) \quad (5)$$

The second derivative of a selected intermediate wavelength is scaled by the other computed second derivative at block 312 by computing a ratio of the two second derivatives. In one embodiment, the attenuation is measured for wavelengths at 680 nm, 720 nm, 760 nm, and 800 nm. The second derivatives of the attenuation spectra are computed at 720 nm and 760 nm and the second derivative at 720 nm is scaled by the second derivative at 760 nm. The scaled second derivative (SD") of the 720 nm attenuation can be expressed as:

$$SD'' = D''(720)/D''(760) \quad (6)$$

This SD"(720) has been found to be dependent on oxygen saturation of the hemoglobin present in the measurement volume but independent of the size of the measurement volume, defined by the optical path of the sensor. Thus, SD"(720) is independent of the total hemoglobin present in the measurement volume and independent of the optical path length. The reduced dependence on total hemoglobin and optical path length is expected to reduce the effects of motion artifact on a measurement of $O_2$Sat based on SD"(720). Measuring attenuation for at least four wavelengths allows the second derivatives of two intermediate wavelengths to be computed, allowing computation of a measurement volume-independent, scaled second derivative.

Once the scaled second derivative is obtained, the stored calibration data is used at block 314 to derive the absolute tissue $O_2$Sat. The second derivative for attenuation at 720 nm wavelength (and 760 nm) is dependent on oxygen saturation and total hemoglobin. Thus, at block 316, HbT may be determined knowing the second derivative of attenuation with respect to wavelength at 720 nm, the derived absolute O2 Sat, and the stored calibration data.

If unequal wavelength spacings are used, a first derivative determined at the numerical center of the unequally spaced wavelengths is first determined. For example, if the wavelengths of 660, 720, 760, and 810 were used, the first derivatives of the attenuation spectra at intermediate wavelengths corresponding to the numerical center of each of these wavelength spacings would be expressed as:

$$\frac{d690}{d\lambda} = \frac{A720 - A660}{720 - 660} = \frac{A720 - A660}{60}$$

$$\frac{d740}{d\lambda} = \frac{A760 - A720}{760 - 720} = \frac{A760 - A720}{40}$$

$$\frac{d785}{d\lambda} = \frac{A810 - A760}{810 - 760} = \frac{A810 - A760}{50}$$

The second derivatives of two intermediate wavelengths occurring at the numerical center between the first derivatives would be computed as:

$$\frac{D715}{d\lambda^2} = \frac{\frac{d740}{d\lambda} - \frac{d690}{d\lambda}}{740 - 690} = \frac{A760 - A720}{2000} - \frac{A720 - A660}{3000}$$

$$\frac{D762.5}{d\lambda^2} = \frac{\frac{d785}{d\lambda} - \frac{d740}{d\lambda}}{785 - 740} = \frac{A810 - A760}{2250} - \frac{A760 - A720}{1800}$$

Based on an assumption of linear scattering, the two second derivatives may be used to compute a scaled second derivative, e.g. D"(715)/D"(762.5) as a volume-independent measure of $O_2$Sat, which can then be used with one of the second derivatives and the calibration data to compute a measure of HbT.

The illustrative equations above which compute the first and second derivatives of the attenuation spectra at the numerical centers of unequal wavelength spacings, and retain the denominators associated with wavelength spacing differences, may be adapted for use with any four selected wavelengths. Selection of different wavelengths will change the calibration constants, and may change the sensitivity of the measurements to $O_2$Sat and HbT and the dependence of the measurements on the tissue measurement volume as defined by the optical pathway of the sensor. Through careful selection of the emitted wavelengths for which attenuation is measured, relatively greater sensitivity to O$_2$Sat and reduced dependence on measurement volume may be obtained.

Oxygen availability, as defined herein, is a function of both oxygen saturation of the hemoglobin present in the measurement volume and the total hemoglobin volume fraction. Depending on the particular monitoring application, the derived tissue O$_2$Sat and HbT may each be used separately in a monitoring algorithm or combined to determine a tissue oxygenation index (TOI) used to monitor a patient's status and/or detect a physiological condition. At block 322, a tissue oxygenation index may be computed as a function of the absolute tissue oxygen saturation and the total hemoglobin volume fraction. For example, a tissue oxygenation index may be a weighted combination of the O$_2$Sat and HbT measurements. Thus, a tissue oxygenation index computed using absolute measurements of O$_2$Sat and HbT can be available on a continuous or periodic basis in an ambulatory patient.

The O$_2$Sat derived from a scaled second derivative is a volume-independent measurement and is therefore expected to have a reduced susceptibility to motion artifact, which could alter the optical pathway and thus alter the measurement volume. However, some embodiments may utilize the measured HbT, which is dependent on the measurement volume, to filter or blank tissue oxygenation monitoring during periods in which HbT is out of a normal range, which may be due to motion or activity of the patient.

Accordingly, in one embodiment, the measured HbT is compared to an acceptable range, e.g. between approximately 1% and 25%, at block 318. If HbT is out of the acceptable range, tissue motion may be causing erroneous HbT measurements. At block 320, the tissue oxygenation measurement is blanked or otherwise deemed invalid based on the out-of-range HbT measurement. For example, patient activity may result in oscillatory movements that produce a signal that is intermittently in and out of the acceptable range. Intervals in which the HbT measurement is out-of-range may be blanked for determining a tissue oxygenation index. During intervals in which the HbT measurement is in range, the tissue oxygenation index is computed at block 322. When HbT is out of range, the absolute tissue oxygen saturation measurement may also be ignored or still be determined and stored since it is a volume-independent measurement.

Alternatively, O$_2$Sat and HbT measurements may be filtered based on the fluctuation of HbT. If HbT variability is low, than a low rate of averaging O$_2$Sat and HbT measurements may be used. If HbT variability increases, an increasing filtering or averaging frequency may be used based on the increased HbT variability.

Figure 10:
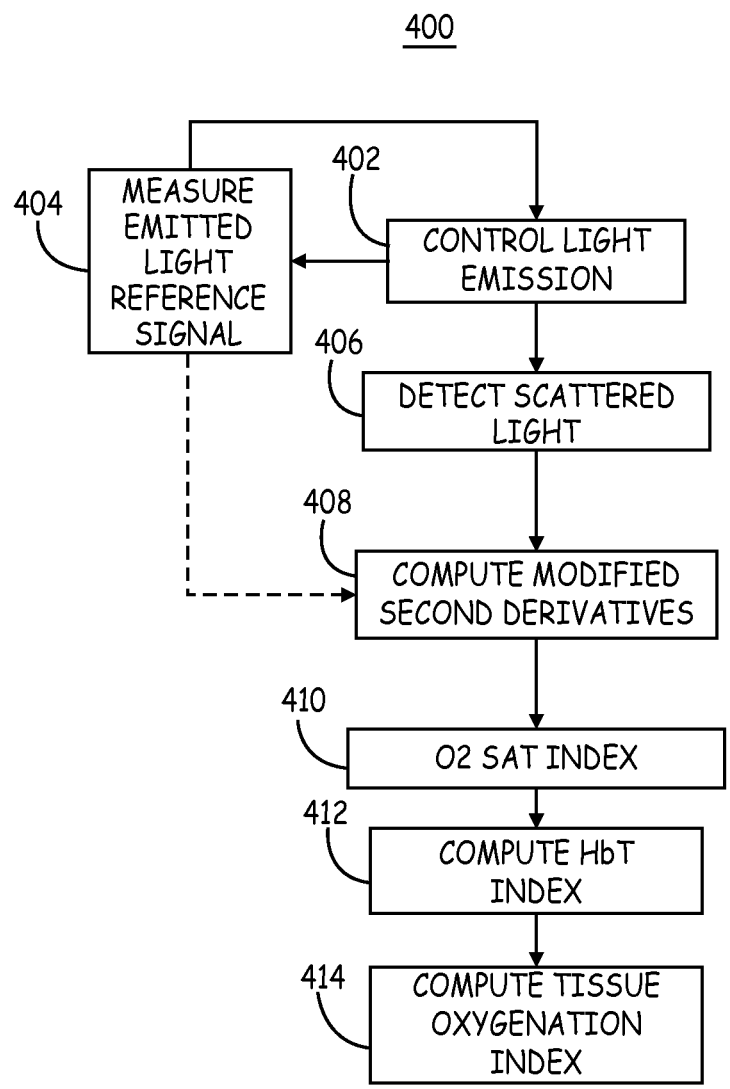
FIG. 10 is a flow chart of an alternative method for using an optical sensor capable of measuring absolute tissue oxygen saturation for monitoring tissue oxygenation.

FIG. 10 is a flow chart of an alternative method 400 for using an optical sensor capable of measuring O$_2$Sat for monitoring tissue oxygenation. At block 402, control signals are applied to drive circuitry to control the emission of light from the light emitting portion of the optical sensor.

In one embodiment, a reference photodetector is included in the light emitting portion to provide a reference signal measuring the emitted light. The intensity of the emitted light may be controlled using a reference feedback signal as indicated by block 404. In the previous method 300 described in conjunction with FIG. 9, a reference photodetector is used to measure the emitted light intensity for computing the attenuation of each wavelength using Equation 3 above. In method 400, the emitted light intensity is measured using the reference photodetector for controlling light emission such that the emitted intensity ($i_{in}$) at each of the wavelengths used for attenuation measurements is maintained within a specified range.

An emitted light reference signal measured at block 404 using the reference photodetector output signal is provided as a feedback signal to the control module controlling light emission at block 402. Drive signals applied to the light emitting portion may be adjusted in response to the emitted light reference signal to maintain the emitted light intensity within a target range for each wavelength selected for attenuation measurements.

When the emitted light is controlled to be maintained within a specified range, the emitted light intensity ($i_{in}$) in the attenuation equation (3) above becomes a constant. Manipulation of the second derivative equation (5) above results in a modified second derivative equation:

$$D''(\lambda_i)_{modified} = C_i - \log(i_{out})_{\lambda,i+1} + 2\log(i_{out})_{\lambda,i} - \log(i_{out})_{\lambda,i-1} \quad (7)$$

which may be rewritten as:

$$D''(\lambda_i)_{modified} = C_i + \log\{(i_{out})_{\lambda,i}^2 / ((i_{out})_{\lambda,i+1})(i_{out})_{\lambda,i-1})\} \quad (8)$$

The term $C_i$ for a given wavelength $\lambda_i$ becomes a calibration constant. Thus, a modified scaled second derivative may be computed using only the detecting portion output signal (and calibration constants $C_i$ determined for each of the measured wavelengths) without using a measurement of emitted light intensity for computing attenuation of the emitted light. In the case where there is no reference measurement for emitted light intensities at each wavelength, but the drive signal to the light sources is controllable, the constants Ci are predetermined functions of the light source drive signal. Note that the above Equation 8 is written for equal wavelength spacings and will include more terms for non-equal wavelength spacings (see Equation 4 above) in which case the denominators in the derivative equations corresponding to wavelength spacing differences need be retained.

The scattered light is detected by the optical sensor at block 406 and used to compute the modified second derivatives at block 408 at two (or more) intermediate wavelengths. The modified second derivatives need only be computed for the two wavelengths being used to compute O$_2$Sat and HbT.

A simplified scaled second derivative may be used as an estimate of O$_2$Sat in which the $C_i$ constants are ignored in the above equations. A simplified scaled second derivative may take the form of:

$$SD'' = \frac{-\log(i_{out})_{\lambda,i+1} + 2\log(i_{out})_{\lambda,i} - \log(i_{out})_{\lambda,i-1}}{-\log(i_{out})_{\lambda,i+2} + 2\log(i_{out})_{\lambda,i+1} - \log(i_{out})_{\lambda,i}} \quad (9)$$

This simplified scaled second derivative may be useful for measuring a non-calibrated, index of tissue oxygen saturation at block 410. A corresponding non-calibrated index of HbT may be computed at block 412 using the simplified second derivative computed using equation 9. The O$_2$Sat and HbT indices may be used individually or combined in a tissue oxygenation index computed as a function of both at block 414.

In addition or alternatively to using the emitted light reference signal as feedback to control light emission, the emitted light reference signal may be used by the monitoring module to adjust the computed modified second derivatives at block 408. Shifts in the intensity of the emitted light may be accounted for by introducing a correction term (CT) in the equation used to compute the modified second derivative. Accordingly, an adjusted modified second derivative for a selected intermediate wavelength used to compute absolute oxygen saturation might be computed using:

$$D''(\lambda_i)_{modified} = C_i - \log(i_{out} + CT)_{\lambda,i+1} + 2\log(i_{out} + CT)_{\lambda,i} - \log(i_{out} + CT)_{\lambda,i-1} \quad (9)$$

wherein CT is a correction term determined for each wavelength using the emitted light reference signal and is used to adjust the remitted light intensities $i_{out}$ for each wavelength.

Figure 11:
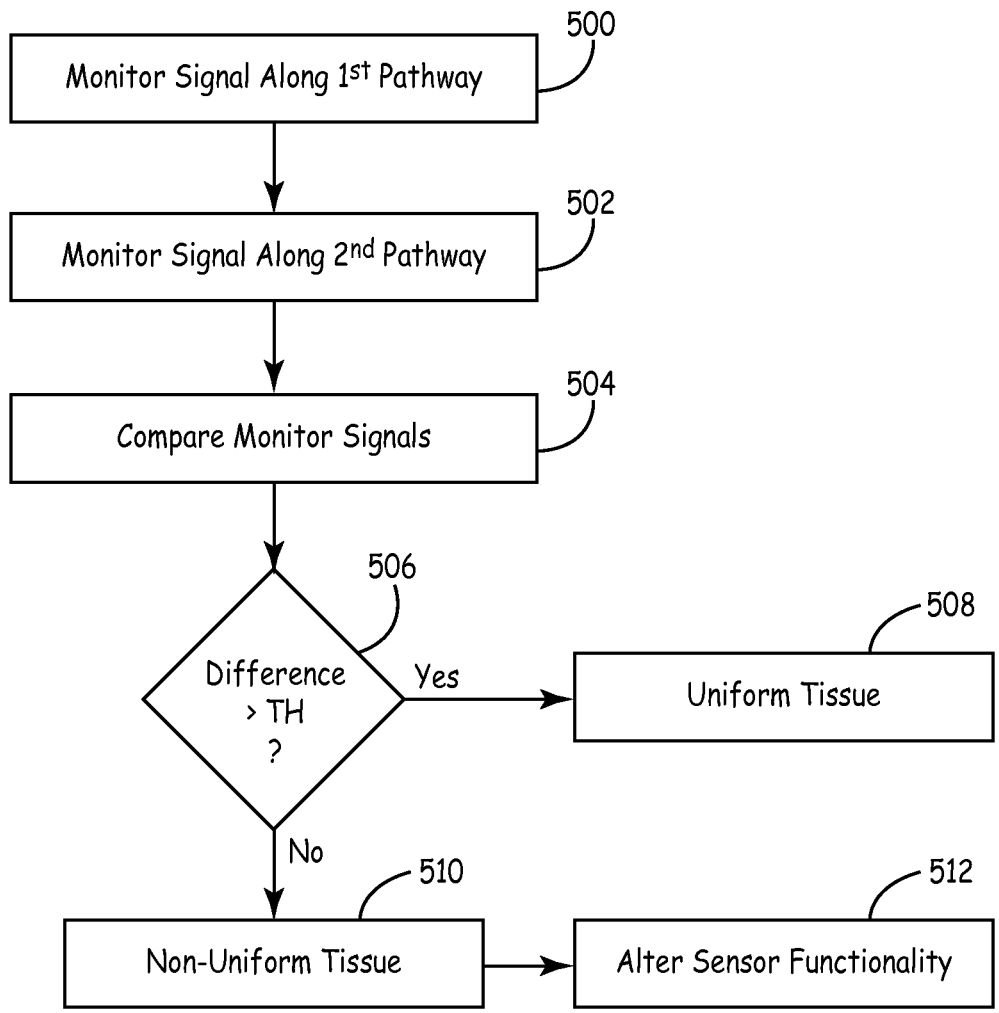
FIG. 11 is a flowchart of a method of monitoring tissue oxygenation in a medical device system.

FIG. 11 is a flowchart of a method of monitoring tissue oxygenation in a medical device system. It is understood that the medical device system described in FIG. 11 may correspond to a system associated with the sensor alone, or may correspond to the sensor being incorporated in an implantable medical device, as shown in FIG. 1D. As described above, it is desirable that the optical sensor be positioned over substantially homogenous tissue, and that obtaining measurements at different tissues depths can be used to provide a measure of tissue uniformity. Therefore, according to one embodiment, in order to obtain measurements at different tissue depths and volumes, the functionality of the modular assemblies 102 and 102' of the optical sensor is chosen to define a first optical pathway 110 and a second optical pathway 112, described above. An $O_2$Sat measurement is determined along the first optical pathway 110, block 500, and an $O_2$Sat measurement is determined along the second optical pathway 112, block 502. The two $O_2$Sat measurements are compared, Block 504, and a determination is made as to whether a difference between the $O_2$Sat measurements is greater than a uniformity threshold, block 506. According to one embodiment, for example, the uniformity threshold is set as a percentage, such as a 2 percent difference. In another embodiment, the uniformity threshold may include multiple thresholds to identify levels of uniformity, such as a first threshold for identifying the tissue as essentially homogenous and a second threshold for identifying the tissue as being nearly homogenous. For example, the first threshold may be set at 2 percent and the second threshold may be set as 5 percent, so that the tissue is identified as being essentially homogenous if it is determined that the difference between the $O_2$Sat measurements is less than 2 percent, and as being nearly homogenous if it is determined that the difference between the $O_2$Sat measurements is not less than 2 percent, but less than 5 percent.

Figure 12:
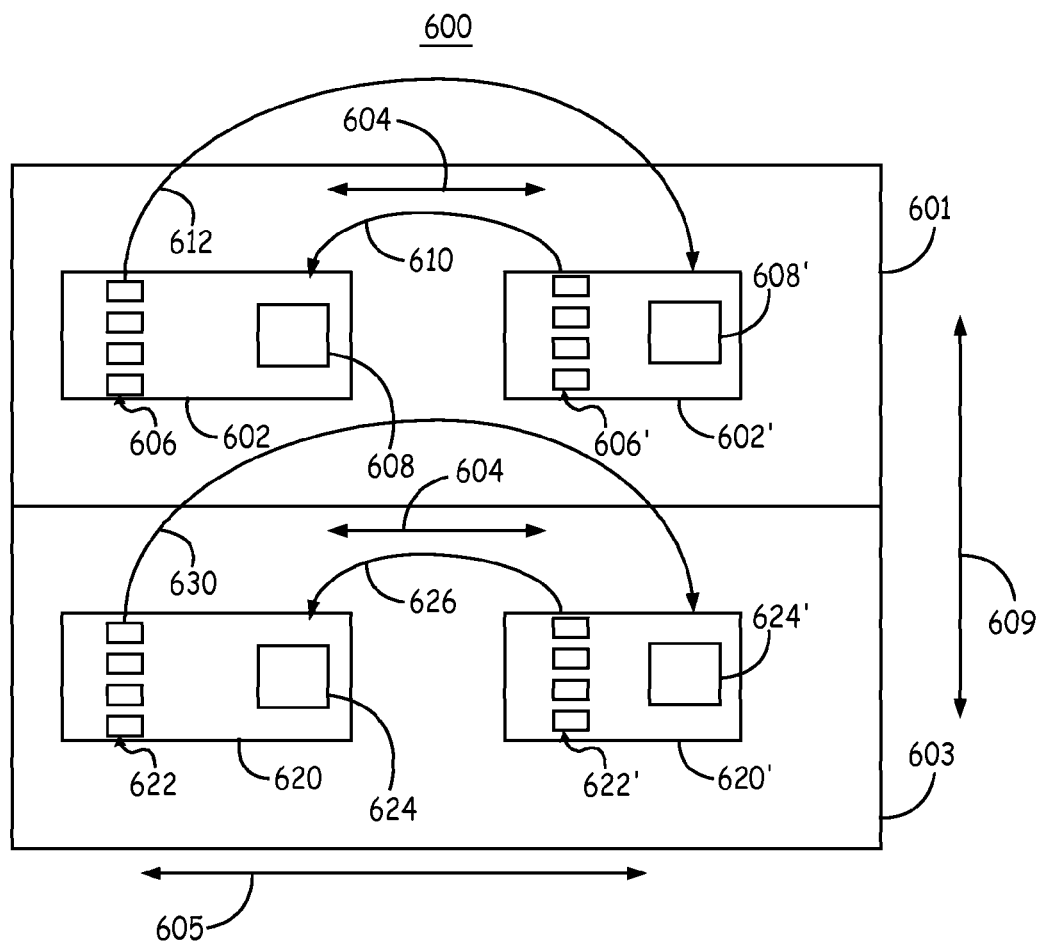
FIG. 12 is a top schematic view of a sensor 600 according to another embodiment.

If the difference between the two $O_2$Sat measurements measured along the two optical pathways 110 and 112 is not greater than the uniformity threshold, the tissue over which the optical sensor is positioned is determined to be homogenous, or uniform, block 508, and the oxygen saturation signal derived from the optical sensor is utilized by the device to confirm detection of a cardiac event. If the difference between the two $O_2$Sat measurements is greater than the uniformity threshold, the tissue over which the optical sensor is positioned is determined to be non-uniform, block 510, and the functionality of the optical sensor is changed, block 512. For example, changing the functionality of the optical sensor may correspond to the optical signal being no longer utilized in the detection process, or in the optical pathways associated with the modular assemblies 102 and 102' being reselected, or reduced to just a single pathway. According to another embodiment, if the tissue is determined to be non-uniform, a determination made be made as to whether the two $O_2$Sat measurements behave similarly FIG. 12 is a top schematic view of a sensor according to another embodiment. As illustrated in FIG. 12, an optical sensor 600 may include four modular assemblies 602, 602', 620, and 620'. Specifically, sensor 600 includes a first portion 601 having assemblies 602 and 602' included therein, with each assembly including light sources 606 and 606' and light detectors 608 and 608', respectively, and a second portion 603 having assemblies 620 and 620' included therein, with each assembly including light sources 622 and 622' and light detectors 624 and 624', respectively. Similar to sensor 100 described above, the functionality of each assembly 602, 602', 620, and 620' is selectable such that one assembly is selected to operate as an emitting portion and the other assembly is selected to operate as a detecting portion. This functional selection may be made at the time of manufacture and not alterable thereafter. Alternatively, this selection may be dynamic under the control of control circuitry included in the associated medical device. Functional selection of the assemblies may be based on user input or in response to feedback or self-diagnostic measurements made by sensor 600.

By arranging the light sources and the light detectors in a particular spatial manner with respect to one another, four different optical pathways 610, 612, 626 and 630, and thus four different measurement volumes, may be realized depending on the selection of the functionality of each assembly. If assembly 602 is selected as the detecting portion and assembly 602' is selected as the emitting portion, the emitting-to-detecting spacing 604 is relatively shorter than a spacing 605 that would result if functional selection of assemblies 602 and 602' were reversed (i.e., assembly 602 selected as emitting and assembly 602' selected as detecting). Similarly, if assembly 620 is selected as the detecting portion and assembly 620' is selected as the emitting portion, the emitting-to-detecting spacing 604 is relatively shorter than a spacing 605 that would result if functional selection of assemblies 620 and 620' were reversed (i.e., assembly 620 selected as emitting and assembly 620' selected as detecting). The resulting longer emitting-to-detecting spacing 605 will result in relatively longer (and deeper) optical pathways 612 and 630 (shown schematically), when assemblies 602 and 620 are emitting light, than the optical pathways 610 and 626 (shown schematically) that results when assemblies 602' and 620' are emitting light.

As such, through proper orientation of assemblies 602, 602', 620, and 620' and the emitting and detecting components therein, different optical pathways may be selected through the selectable functionality of the assemblies 602, 602', 620, and 620', including variable spacing for variable tissue depths.

Figure 13:
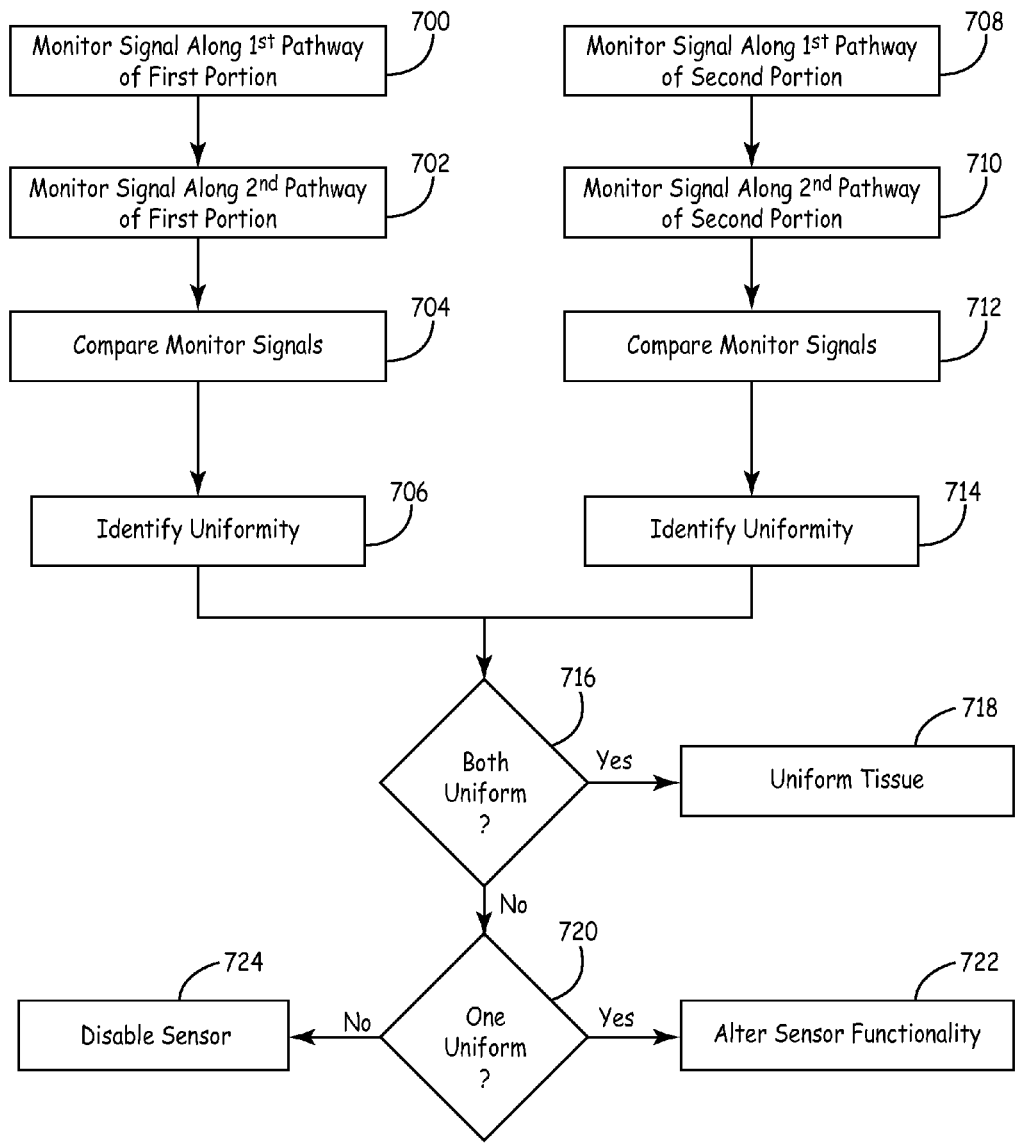
FIG. 13 is a flowchart of a method of monitoring tissue oxygenation in a medical device system.

FIG. 13 is a flowchart of a method of monitoring tissue oxygenation in a medical device system. According to an embodiment, the use of multiple sensor assemblies enables the device to better account for the effects on the optical sensor that may occur as a result of undesired movement of the sensor, or due to motion or posture changes of the patient. Therefore, according to one embodiment, in order to account for motion effects on the sensor, the functionality of the modular assemblies 602, 602', 620, and 620' of the optical sensor is chosen to define respective first optical pathways 610 and 626 and second optical pathways 612 and 630, described above.

In the example illustrated in FIG. 12, the first optical pathways 610 and 626 have approximately equal emitting-to-detecting spacing 604, and are laterally spaced a distance 609 from each other. Similarly, the second optical pathways 612 and 630 have approximately equal emitting-to-detecting spacing 605, and are also laterally spaced distance 609 from each other. In this way, sensor 600 is able to determine variations in $O_2$Sat measurements along two separate perpendicular pathways through tissue to detect variations in tissue uniformity extending both laterally in the direction of arrow 609, and laterally in the direction of arrow 605, along sensor 600. This multi-dimensional sensing increases the ability of the device to better account for effects on sensor 600 due to undesired motion or drift of the sensor 600, or due to motion or posture changes of the patient.

For example, if the uniformity of tissue between modules 602 and 602' changes by a significant amount, while the uniformity of tissue between modules 620 and 620' remains relatively constant, it is likely that either shifting or drift of the sensor 600 or motion of the patient has occurred. A determination can then be made as to whether the sensor 600 can continue to be utilized using the O$_2$Sat measurement from both portions 601 and 603 of the sensor 600, using only the O$_2$Sat measurement from one of the two portions 601 and 603, i.e., portion 603 in this example, or if the sensor 600 should be disabled or re-positioned. In addition, an alert may be delivered to indicate possible drift of the sensor 600 to the patient or clinician.

For example, as illustrated in FIG. 13, in order to determine tissue uniformity, an O$_2$Sat measurement is determined for both the first portion 601 and the second portion 603 of the sensor 600. In particular, an O$_2$Sat measurement is determined, block 700, along the first optical pathway 610 of the first portion 601 and along the second optical pathway 612 of the first portion 601 of sensor 600, block 702. The two O$_2$Sat measurements are compared, Block 704, and a uniformity is identified for the first portion 601 of the sensor 600, block 706.

For example, in order to identify the uniformity for the first portion 601 of the sensor 600, a determination is made in block 706 as to whether a difference between the two O$_2$Sat measurements for the first portion 601 is greater than a uniformity threshold. If the difference between the two O$_2$Sat measurements measured along the two optical pathways 610 and 612 is not greater than the uniformity threshold, the tissue over which the first portion 601 of the optical sensor is positioned is determined to be homogenous, or uniform in block 706. If the difference between the two O$_2$Sat measurements is greater than the uniformity threshold, the tissue over which the first portion 601 of the optical sensor is positioned is determined to be non-uniform in block 706.

Similarly, an O$_2$Sat measurement is determined, block 708, along the first optical pathway 626, and along the second optical pathway 630 of the second portion 601 of the sensor 600, block 710. The two O$_2$Sat measurements are compared, Block 712, and a uniformity is identified for the second portion 603 of the sensor 600, block 714.

For example, in order to identify the uniformity for the second portion 603 of the sensor 600, a determination is made in block 714 as to whether a difference between the two O$_2$Sat measurements for the second portion 603 is greater than the uniformity threshold. If the difference between the two O$_2$Sat measurements measured along the two optical pathways 626 and 630 is not greater than the uniformity threshold, the tissue over which the second portion 603 of the optical sensor is positioned is determined to be homogenous, or uniform in block 714. If the difference between the two O$_2$Sat measurements is greater than the uniformity threshold, the tissue over which the second portion 603 of the optical sensor is positioned is determined to be non-uniform in block 714.

Once a uniformity has been identified for both the first portion 601 and the second portion 603 of the sensor 600, a determination is made as to whether both portions 601 and 603 of the sensor 600 are positioned over uniform tissue, block 716. If both the first portion 601 and the second portion 603 are identified as uniform, block 718, the oxygen saturation signal derived from both portions 601 and 603 of the sensor 600 is utilized to confirm detection of a cardiac event by the device. If both the first portion 601 and the second portion 603 are not identified as uniform, a determination is made as to whether one of the first portion 601 and the second portion 603 is uniform, block 720.

If one of the first portion 601 and the second portion 603 is uniform, the functionality of the sensor 600 is changed, block 722, and the sensor 600 operates under the new functionality. For example, changing the functionality may include disabling the sensor altogether, or may include continuing to utilize the sensor 600 using only the portion determined to be positioned over uniform tissue. In addition, in either condition, an alert may be generated to indicate to the patient or clinician that a change in the uniformity of the tissue over which the sensor is positioned, or in the quality of the measurement has occurred. If one of the first portion 601 and the second portion 603 is not uniform, i.e., both portions 601 and 603 are positioned over non-uniform tissue, the sensor 600 is disabled, 724, and/or an alert may be generated to indicate to the patient or clinician that a change in the uniformity of the tissue over which the sensor is positioned, or in the quality of the measurement has occurred.

Thus, a medical device and associated methods have been presented in the foregoing description with reference to specific embodiments. It is appreciated that various modifications to the referenced embodiments may be made without departing from the scope of the disclosure as set forth in the following claims.

The invention claimed is:

1. A method of detecting signals in a medical device, comprising:
   detecting emitted light scattered by a volume of tissue delivered along a first pathway to generate corresponding first detected light intensity output signals;
   detecting emitted light scattered by the volume of tissue delivered along a second pathway different from the first pathway to generate corresponding second detected light intensity output signals;
   determining whether a difference between the emitted light detected along the first pathway and the emitted light detected along the second pathway is greater than a predetermined threshold; and
   altering sensing by the device in response to the determining whether a difference is greater than the predetermined threshold.

2. The method of claim 1, further comprising:
   determining a first oxygen saturation measurement corresponding to detected light emitted along the first pathway in response to the first detected light intensity output signals; and
   determining a second oxygen saturation measurement corresponding to detected light emitted along the second pathway in response to the second detected light intensity output signals, wherein determining whether a difference between the emitted light detected along the first pathway and the emitted light detected along the second pathway is greater than a predetermined threshold comprises comparing the first and second oxygen saturation measurement.

3. The method of claim 2, wherein altering sensing by the device comprises selecting between the first pathway and the second pathway.

4. The method of claim 2, wherein determining whether a difference between the emitted light detected along the first pathway and the emitted light detected along the second pathway is greater than a predetermined threshold comprises determining levels of uniformity of the volume of tissue.

5. The method of claim 4, wherein determining whether a difference between the emitted light detected along the first pathway and the emitted light detected along the second pathway is greater than a predetermined threshold comprises:

determining whether a difference between the emitted light detected along the first pathway and the emitted light detected along the second pathway is less than a first level threshold;

identifying the volume of tissue as having a first tissue uniformity in response the difference being less than the first level threshold;

determining whether a difference between the emitted light detected along the first pathway and the emitted light detected along the second pathway is greater than a second level threshold different from the first level threshold; and identifying the volume of tissue as having a second tissue uniformity in response the difference being both less than the second level threshold and not less than the first level threshold.

6. The method of claim 5, wherein altering sensing by the device comprises selecting between the first pathway and the second pathway in response to the identifying.

7. The method of claim 1, wherein determining whether a difference between the emitted light detected along the first pathway and the emitted light detected along the second pathway is greater than a predetermined threshold comprises:

determining an attenuation measurement for each wavelength of a plurality of wavelengths of the first pathway and the second pathway in response to the first and second detected light intensity output signals;

determining a second derivative of the attenuation measurement for a first wavelength and a second wavelength of a plurality of wavelengths corresponding to the first pathway in response to only the first detected light intensity output signals;

determining a second derivative of the attenuation measurement for a first wavelength and a second wavelength of a plurality of wavelengths corresponding to the second pathway in response to only the second detected light intensity output signals;

determining a first oxygen saturation measurement corresponding to detected light emitted along the first pathway in response to the determined second derivative associated with the first pathway;

determining a second oxygen saturation measurement corresponding to detected light emitted along the second pathway in response to the determined second derivative associated with the second pathway; and comparing the first and second oxygen saturation measurement.

8. The method of claim 7, wherein determining whether a difference between the emitted light detected along the first pathway and the emitted light detected along the second pathway is greater than a predetermined threshold comprises determining levels of uniformity of the volume of tissue.

9. The method of claim 8, wherein determining whether a difference between the emitted light detected along the first pathway and the emitted light detected along the second pathway is greater than a predetermined threshold comprises:

determining whether a difference between the emitted light detected along the first pathway and the emitted light detected along the second pathway is less than a first level threshold;

identifying the volume of tissue as having a first tissue uniformity in response the difference being less than the first level threshold;

determining whether a difference between the emitted light detected along the first pathway and the emitted light detected along the second pathway is greater than a second level threshold different from the first level threshold; and identifying the volume of tissue as having a second tissue uniformity in response the difference being both less than the second level threshold and not less than the first level threshold.

10. The method of claim 9, wherein altering sensing by the device comprises selecting between the first pathway and the second pathway in response to the identifying.

11. The method of claim 1, wherein determining whether a difference between the emitted light detected along the first pathway and the emitted light detected along the second pathway is greater than a predetermined threshold comprises:

determining an attenuation measurement for each wavelength of a plurality of wavelengths of the first pathway and the second pathway in response to the first and second detected light intensity output signals;

determining a second derivative of the attenuation measurement for a first wavelength and a second wavelength of a plurality of wavelengths corresponding to the first pathway in response to only the first detected light intensity output signals;

determining a second derivative of the attenuation measurement for a first wavelength and a second wavelength of a plurality of wavelengths corresponding to the second pathway in response to only the second detected light intensity output signals;

determining a scaled second derivative of the attenuation measurement of the first wavelength for the first pathway using the determined second derivative of the attenuation of the second wavelength for the first pathway;

determining a first oxygen saturation measurement corresponding to detected light emitted along the first pathway in response to the determined scaled second derivative for the first pathway;

determining a scaled second derivative of the attenuation measurement of the first wavelength for the second pathway using the determined second derivative of the attenuation of the second wavelength for the second pathway;

determining a second oxygen saturation measurement corresponding to detected light emitted along the first pathway in response to the determined scaled second derivative for the second pathway; and comparing the first and second oxygen saturation measurement.

12. A non-transitory computer readable medium having computer executable instructions for performing a method comprising:

detecting emitted light scattered by a volume of tissue delivered along a first pathway at a plurality of wavelengths to generate corresponding first detected light intensity output signals;

detecting emitted light scattered by the volume of tissue delivered along a second pathway different from the first pathway at a plurality of wavelengths to generate corresponding second detected light intensity output signals;

determining whether a difference between the emitted light detected along the first pathway and the emitted light detected along the second pathway is greater than a predetermined threshold; and altering sensing by the device in response to the determining whether a difference is greater than the predetermined threshold.

* * * * *